United States Patent [19]

Kurozumi et al.

[11] 4,180,672
[45] Dec. 25, 1979

[54] 2-ORGANOTHIO-2-CYCLOPENTENONES, ORGANOTHIO-CYCLOPENTANES DERIVED THEREFROM

[75] Inventors: Seizi Kurozumi; Takeshi Toru; Makiko Kobayashi, all of Hino; Yoshinobu Hashimoto, Fuzisawa, all of Japan

[73] Assignee: Teijin Limited, Osaka, Japan

[21] Appl. No.: 775,119

[22] Filed: Mar. 7, 1977

[30] Foreign Application Priority Data

Aug. 13, 1976 [JP] Japan .................................. 51-96107
Aug. 13, 1976 [JP] Japan .................................. 51-96108
Aug. 13, 1976 [JP] Japan .................................. 51-96109
Nov. 19, 1976 [JP] Japan .................................. 51-138380
Dec. 1, 1976 [JP] Japan .................................. 51-143294

[51] Int. Cl.² .............................................. C07C 177/00
[52] U.S. Cl. .................................. 560/15; 260/315.8 P; 260/159 P; 260/347.8; 260/749.55; 260/399; 260/448.8 R; 260/586 R; 260/406; 560/9; 560/17; 560/118; 560/121; 562/496; 562/503; 474/303; 474/308; 474/317
[58] Field of Search ................. 260/514 D; 560/121, 560/9, 15, 118; 562/426, 500, 503

[56] References Cited

U.S. PATENT DOCUMENTS 4,018,820   4/1977   Fried .................................. 260/514
4,080,458   3/1978   Raduvz et al. ..................... 424/263

OTHER PUBLICATIONS

McOmie, Protective Groups in Organic Chemistry, pp. 332-333, (1973).

Primary Examiner—Robert Gerstl
Attorney, Agent, or Firm—Sherman & Shalloway

[57] ABSTRACT

Organothiocyclopentanes of the formula

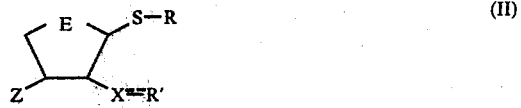

wherein E represents $>C=O$ or

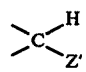

in which Z' represents a hydrogen atom, a hydroxyl group or a protected hydroxyl group; X represents —S—, —CH$_2$—, —CH=; = represents a single or double bond; R' represents a monovalent or divalent organic group containing 1 to 25 carbon atoms; R represents a monovalent organic group containing 1 to 25 carbon atoms; Z represents a hydrogen atom, a hydroxyl group or a protected hydroxyl group; and when both E and Z represent a hydroxyl group or a protected hydroxyl group, X represents —S—.

Also, 2-organothio-2-cyclopentenones of the formula

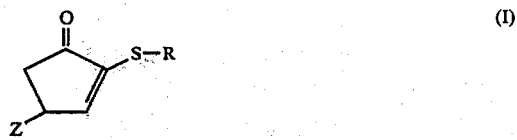

wherein R and Z are as defined above.

The compounds of formula (I) are prepared by reacting 2,3-epoxy-cyclopentanone or its derivatives with mercaptans in the presence of basic compounds. The compounds of formula (II) are prepared by reacting the compounds of formula (I) with mercaptans or organocopper-lithium compounds, and optionally reducing the resulting products, and optionally protecting the hydroxyl group at their cyclopentane ring.

The compounds of formula (I) have an action of inhibiting ulcer formation, and are useful intermediates for the compounds of formula (II). The compounds of formula (II) are monothia- or dithia-prostanoic acid derivatives, and exhibit various superior pharmacological actions.

3 Claims, No Drawings

2-ORGANOTHIO-2-CYCLOPENTENONES, ORGANOTHIO-CYCLOPENTANES DERIVED THEREFROM

This invention relates to novel 2-organothio-2-cyclopentenones, novel organothiocyclopentanes derived therefrom, and processes for producing these compounds.

The novel 2-organothio-2-cyclopentenones of the invention are compounds expressed by the following formula

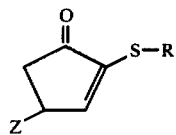

wherein R is a monovalent organic group containing 1 to 25 carbon atoms, and Z is a hydrogen atom, a hydroxyl group or a protected hydroxyl group.

The novel organothiocyclopentanes of the invention are compounds expressed by the following formula

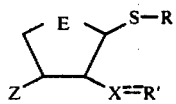

wherein E represents >C=O or

in which Z' represents a hydrogen atom, a hydroxyl group or a protected hydroxyl group; X represents —S—, —CH$_2$—, —CH=; ==== represents a single or double bond; R' represents a monovalent or divalent organic group containing 1 to 25 carbon atoms; R represents a monovalent organic group containing 1 to 25 carbon atoms; Z represents a hydrogen atom, a hydroxyl group or a protected hydroxyl group; and when both E and Z represent a hydroxyl group or a protected hydroxyl group, X represents —S—.

According to the present invention, the novel 2-organothio-2-cyclopentenones of formula (I) have useful physiological activities such as an anti-inflammatory action, and can be converted to the novel organothiocyclopentanes of formula (II), i.e., thia- or dithio-prostanoic acid derivatives, which have specific physiological activities and are useful as medicines.

In recent years, prostaglandins have found a wide range of applications as medicines. Some synthetic prostaglandins are known to have specific physiological activities, and are expected to be useful as drugs. [See, for example, E. Horton et al., New Scientist, Jan. 1st, 9 (1976)] It has recently been found that prostaglandin analogs in which the carbon atoms constituting the prostanoid skeleton are replaced by hetero atoms, for example, thiaprostanoids, show specific physiological activities and act as prostaglandin agonists or antagonists. [J. Fried et al., J. Amer. Chem. Soc., 96, 6759 (1974); I. Vlattas et al., Tetrahedron Letters 4459 (1974), J. Amer. Chem. Soc., 98, 2008 (1976), and Belgian Pat. No. 828925 owned by Merck Co. (1975)].

E-type prostanoic acid derivatives in which a side chain is bonded at the 2-position of the cyclopentanone ring through a sulfur atom have not been known heretofore, and no method for their production has been known either.

According to the present invention, the 2-organothio-2-cyclopentenones of the formula (I) can be produced by epoxidizing cyclopentenone or its derivative of the following formula

wherein Z represents a hydrogen atom, a hydroxyl group or a protected hydroxyl group, in a manner known per se to form 2,3-epoxycyclopentanone or its derivative of the following formula

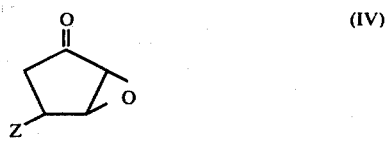

wherein Z is as defined above, and then reacting the resulting compound with a mercaptan of the following formula

wherein R represents a monovalent organic group containing 1 to 25 carbon atoms, in the presence of a basic compound.

As far as the present inventors know, the 2,3-epoxycyclopentanone derivatives of formula (IV) (Z is a hydroxyl group or a protected hydroxyl group) produced in the course of the above synthesis are also novel compounds not described in the literature, and are useful intermediates for the preparation of the 2-organothio-2-cyclopentenones of formula (I).

The organothiocyclopentanes of formula (II) derived from the 2-organothio-2-cyclopentenones of formula (I), according to the definition of X, embrace diorganothiocyclopentanes of the following formula

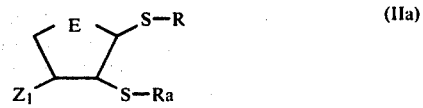

wherein E is as defined hereinabove; R and Ra are identical to or different from each other, and each represents a monovalent organic group containing 1 to 25 carbon atoms; and Z$_1$ is identical to or different from Z, and represents a hydrogen atom, a hydroxyl group or a protected hydroxyl group;

and organothiocyclopentanes of the following formula

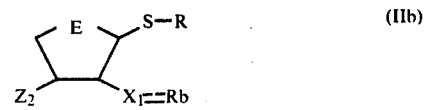

wherein E is as defined above; $Z_2$ represents a hydrogen atom, a hydroxyl group or a protected hydroxyl group, with the proviso that when E is

and Z' represents a hydroxyl group or a protected hydroxyl group, $Z_2$ represents a hydrogen atom; R is as defined hereinabove; $X_1$ represents —$CH_2$— or —CH⩭; ⩭ represents a single or double bond according to the definition of $X_1$; and Rb represents a monovalent or divalent organic group containing 1 to 25 carbon atoms according to the definition of $X_1$.

According to the present invention, the diorganothiocyclopentanes of formula (IIa) can be produced by reacting a 2-organothio-2-cyclopentenone of formula (I) with a mercaptan of the following formula $$HSR'a \qquad (Va)$$

wherein R'a is identical to or different from R, and represents a monovalent organic group containing 1 to 25 carbon atoms,
in the presence or absence of a basic compound to form a diorganothiocyclopentanone of the following formula

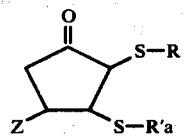
(IIa')

wherein R, Z and R'a are as defined above, optionally reducing this compound to a diorganothiocyclopentanol, and then optionally converting the hydroxyl group substituted at its cyclopentane ring to a protected hydroxyl group in a manner known per se.

According to the present invention, the organothiocyclopentanes of formula (IIb) can be prepared by reacting a 2-organothio-2-cyclopentenone of formula (I) with an organocopper lithium compound of the following formula $$LiCu(-X_1 \mathrel{\underline{\underline{=\!=}}} R'b)_p Q_{2-p} \qquad (VI)$$

wherein $X_1$ is as defined above; R'b represents a monovalent or divalent organic group optionally having a substituent inert to an organolithium compound; ⩭ is as defined above; Q represents a monovalent organic or inorganic group; and p is 1 or 2,
in the presence of an aprotic inert organic solvent to form an organothiocyclopentanone of the following formula

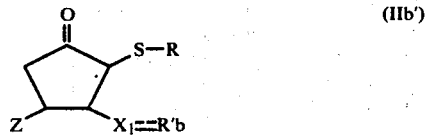
(IIb')

wherein all symbols are as defined hereinabove, optionally reducing this compound when Z is a hydrogen atom, to form an organothiocyclopentanol, and then optionally converting the hydroxyl group substituted at its cyclopentane ring to a protected hydroxyl group in a manner known per se.

The manufacturing processes described above can be schematically shown as follows:

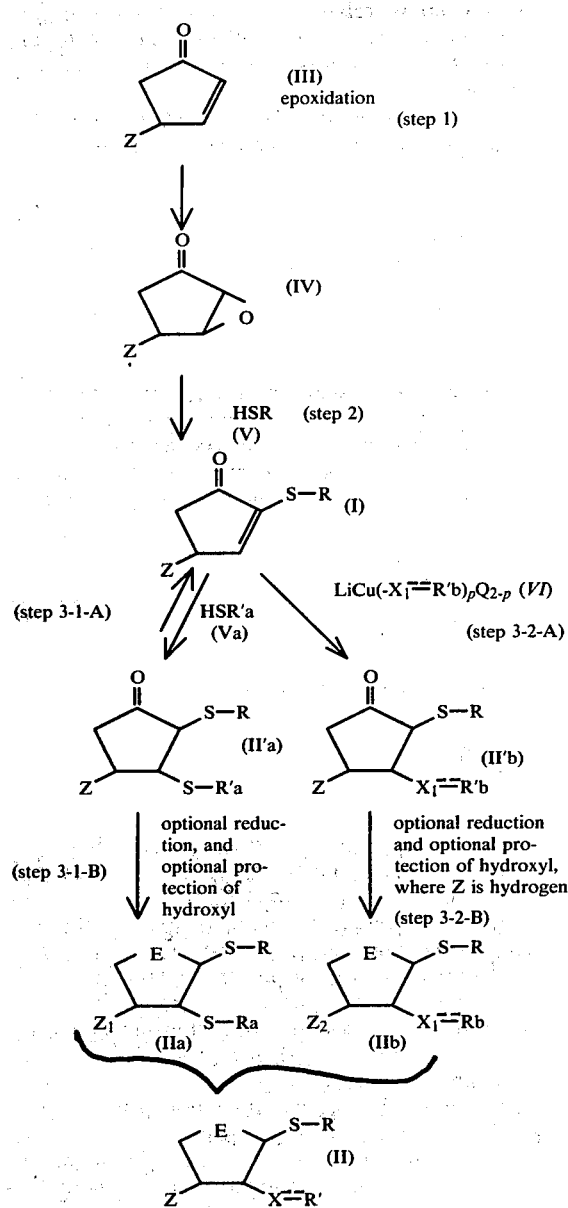

As can be seen from the above scheme, the 2-organothio-2-cyclopentenones of formula (I) are key intermediates for the production of the organothiocyclopentanes of formulae (IIa and IIb) of the invention having useful physiological activities as medicines, and possess by themselves useful physiological activities as will be described hereinbelow.

The steps shown in the above scheme are described below in greater detail.

1. Step 1 (epoxidation)

The cyclopentenone derivatives of formula (III) used as starting materials in the process of this invention may be optically active compounds or racemic ones. A process for producing them from 3,5-diacetoxycyclopentene is disclosed, for example, in west German Laid-Open Specification DT-OS 2558190.

Z in formula (III) represents a hydrogen atom, a hydroxyl group or a protected hydroxyl group. Suitable hydroxyl-protecting groups are organosilyl groups such as t-butyldimethylsilyl, trimethylsilyl or tribenzylsilyl, and groups forming an ether linkage together with the oxygen atom of the hydroxyl group, such as 2-tetrahydropyranyl, 2-tetrahydrofuranyl or 1-ethoxyethyl.

The epoxidation in step 1 is performed by reacting the cyclopentenone derivatives, for example, with hydrogen peroxide in the presence of basic compounds. Suitable basic compounds are inorganic bases such as sodium hydroxide or potassium hydroxide. The amount of the basic compound is 1 to 100 moles, preferably 2 to 20 moles, per mole of the cyclopentenone derivative. Usually, such a basic compound is used as an aqueous solution having a concentration of 0.5 to 5 N, preferably 0.5 to 3 N.

Normally, hydrogen peroxide is used as an aqueous solution having a concentration of about 10 to 90%, especially 20 to 50%. The amount of hydrogen peroxide used is 1 to 200 moles, preferably 2 to 100 moles, per mole of the cyclopentenone derivative.

In order to cause the reaction to proceed smoothly, it is preferably carried out in the presence of an inert organic solvent. Suitable solvents are water-miscible solvents, for example, alcohols such as methyl alcohol, ethyl alcohol, propyl alcohol or butyl alcohol, and ethers such as tetrahydrofuran, dioxane or dimethoxyethane. The amount of the organic solvent used is 1 to 200 times, preferably 3 to 100 times, the volume of the cyclopentenone derivative.

The reaction easily proceeds under mild conditions, and therefore, is carried out at $-10°$ to $100°$ C., preferably $0°$ to $60°$ C.

The reaction time differs according to the reaction temperature and the reaction solvent used. Periods of 1 minute to 30 hours, preferably 15 minutes to 15 hours, are sufficient.

The end point of the reaction is the point at which the starting cyclopentenone derivative has disappeared. This can be determined by such means as thin-layer chromatography.

Preferably, the reaction mixture after the reaction is neutralized with water in the presence of a salt such as ammonium chloride or ammonium sulfate, and extracted with a water-immiscible organic solvent such as diethyl ether. The organic layer is washed with a saturated aqueous solution of ammonium chloride and a saturated aqueous solution of sodium chloride, dried, and concentrated. Purification of the crude product by such means as thin-layer chromatography or column chromatography can afford the epoxycyclopentanone derivatives of formula (IV) having a high purity.

Specific examples of the epoxycyclopentanone derivatives obtained by the present invention include:

4-t-butyldimethylsiloxy-2,3-epoxycyclopentan-1-one,
4-trimethylsiloxy-2,3-epoxycyclopentan-1-one,
4-tribenzylsiloxy-2,3-epoxycyclopentan-1-one,
4-(2-tetrahydropyranyloxy)-2,3-epoxycyclopentan-1-one,
4-(1-ethoxyethyl)-2,3-epoxycyclopentan-1-one,
4-(2-tetrahydrofuranyloxy)-2,3-epoxycyclopentan-1-one, and
4-hydroxy-2,3-epoxycyclopentan-1-one.

2. Step 2 (introduction of an organothio group)

According to the present invention, the 2-organothio-2-cyclopentenones of formula (I) can be produced by reacting the 2,3-epoxy-cyclopentanone or its derivatives of formula (IV) with mercaptans of formula (V) in the presence of basic compounds.

Of these 2-organothio-2-cyclopentenones, those of the following formula

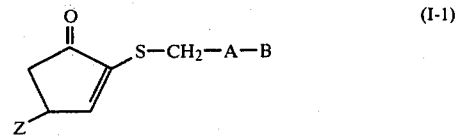
(I-1)

wherein A represents a saturated or unsaturated divalent hydrocarbon group containing 1 to 13 carbon atoms which optionally contains a hydroxyl group or a protected hydroxyl group as a substituent; B represents the group of the following formula $$-(COOR_1)_n \qquad (i)$$

in which $R_1$ represents a hydrogen atom or a saturated or unsaturated aliphatic hydrocarbon group and n is 1 or 0, or the group of the following formula $$-Y-A_1-(COOR_1)_n \qquad (ii)$$

in which Y represents —O— or —S—, $A_1$ represents a divalent saturated or unsaturated aliphatic hydrocarbon group containing 1 to 3 carbon atoms, $R_1$ and n are as defined above with respect to formula (i), with the proviso that when n is 0, —$COOR_1)_n$ represents a hydrogen atom; and Z is as defined hereinabove, are especially useful because they themselves possess specific physiological activities, and can be converted to organothiocyclopentanes of formula (II) having especially high physiological activities.

It has previously been known that nucleophilic reagents cleave the oxide ring of 2,3-dpoxycyclohexanone to afford 2-substituted cyclohexenone derivatives [see M. A. Tobias et al., J. Org. Chem., 35, 1709 (1970)]. The reaction of 2,3-epoxycyclopentanone or its 4-substituted (Z)-2,3-epoxycyclopentanone derivatives of formula (IV) with thiols to give organothiocyclopentenone derivatives, as in step 2 of the process of this invention, and the organothiocyclopentenone derivatives formed have not been known.

Suitable bases used in the reaction of step 2 include alkali metal hydroxides or carbonates such as sodium hydroxide, potassium hydroxide, potassium carbonate, and sodium carbonate; and organic bases, for example, tertiary amines such as trimethylamine, triethylamine and pyridine, strong bicyclo bases such as diazabicyclo[2,2,2]octane or diazabicyclo[3,4,0]nonene, and quaternary ammonium compounds such as benzyltrimethyl ammonium hydroxide. Of these, the tertiary amines, above all triethylamine, are preferred.

In order to cause the reaction of step 2 to proceed better, it is preferred to use an inert solvent. Any inert solvent capable of dissolving the starting compound can be used. Suitable solvents include alcohols such as methanol and ethanol, ethers such as diethyl ether and tetrahydrofuran, and hydrocarbons such as hexane and benzene. The amount of the solvent is the one sufficient to cause the reaction to proceed smoothly. Usually, the amount of the solvent is 1 to 100 times, preferably 2 to 20 times, the volume of the starting compound.

Preferably, the mercaptan of formula (V) is used in an amount stoichiometrically equimolar to the starting compound.

The base which catalyzes the reaction is used in an amount of usually 0.001 to 20 moles, preferably 0.1 to 2 moles, per mole of the starting compound.

The feasible reaction temperature is $-20°$ to $100°$ C. Since the reaction is sometimes exothermic, temperatures of $0°$ to $30°$ C. are preferred. The disappearance of the starting compound is regarded as the end point of the reaction. This is observed usually by gas chromatography or thin-layer chromatography, etc. Normally, the reaction ends in 20 minutes to 2 hours. The reaction proceeds faster the higher the reaction temperature, and when the reaction temperature is relatively low, the reaction proceeds slowly.

After the reaction, the 2-organothio-2-cyclopentenone derivative of formula (I) is separated and purified by treating the reaction mixture in a customary manner such as extraction, washing, distillation, chromatography, or combinations of these.

The mercaptan used in the reaction of step 2 is any compound of the formula $$HSR \qquad (V)$$

wherein R is a monovalent organic group containing 1 to 25 carbon atoms.

The organic group R may be saturated or unsaturated and contain an aliphatic or aromatic group. Furthermore, the organic group R may contain a hetero atom such as an oxygen, nitrogen or sulfur atom in the main chain or in the substituent. Accordingly, the substituent may be an oxygen- or sulfur-containing group such as a hydroxyl group, a protected hydroxyl group, a carboxyl group, an ester group, an alkoxy group, or a thiocarboxyl group. Furthermore, the organic group R may contain a group which is less reactive with an epoxy group than a thiol group, such as an alkyl group or a halogen atom.

As stated hereinabove, the mercaptans of formula (V) may be any mercaptans which are stable to the strong bases used as catalyst in the reaction of step 2. The organic group R in the mercaptans may be any organic group, whether saturated or unsaturated, and may contain a wide variety of substituents which are less reactive than the epoxycyclopentanones of formula (IV). In view of the physiological activities of the resulting compounds, mercaptans of the following formula are preferred.

$$HS-CH_2-A-B \qquad (V-1)$$

wherein A represents a saturated or unsaturated divalent hydrocarbon group containing 1 to 13 carbon atoms optionally containing a hydroxyl group or a protected hydroxyl group as a substituent; B represents the group of the formula $$-(-COOR_1)_n \qquad (i)$$

in which $R_1$ represents a hydrogen atom, or a saturated or unsaturated aliphatic hydrocarbon group containing 1 to 10 carbon atoms, and n is 0 or 1, or the group of the formula $$-Y-A_1-(-COOR_1)_n \qquad (ii)$$

in which Y is $-O-$ or $-S-$, $A_1$ represents a divalent saturated or unsaturated aliphatic hydrocarbon residue containing 1 to 3 carbon atoms, and $R_1$ and n are as defined with regard to formula (i), eith the proviso that when n is 0, $-(-COOR_1)_n$ represents a hydrogen atom.

The use of the mercaptans of formula (V-1) can afford preferred 2-organothio-2-cyclopentenones of formula (I-1) given hereinabove.

Especially preferred species of the mercaptans of formula (V) are those expressed by the following formulae (V-2) and (V-3) below:

$$HS-CH_2-A_2-(-COOR_1)_n \qquad (V-2)$$

wherein $A_2$ represents a saturated or unsaturated divalent aliphatic hydrocarbon group containing 1 to 13 carbon atoms optionally containing a hydroxyl group or a protected hydroxyl group; $R_1$ represents a hydrogen atom or a saturated or unsaturated aliphatic hydrocarbon group containing 1 to 10 carbon atoms; and n is 1 or 0, and when n is 0, $-(-COOR_1)_n$ represents a hydrogen atom.

$$HS-A_3-\phi \qquad (V-3)$$

wherein $A_3$ represents a saturated divalent aliphatic hydrocarbon group containing 1 to 5 carbon atoms optionally containing a hydroxyl group or a protected hydroxyl group as a substituent; and $\phi$ represents a phenyl, cyclohexyl or cyclopentyl group optionally containing 1 or 2 trifluoromethyl groups, hydroxyl groups, halogen atom, or groups of the formula $-A_1-(-COOR_1)_n$ or $-Y-A_1-(-COOR_1)_n$ in which $A_1$ represents a divalent saturated or unsaturated aliphatic hydrocarbon group containing 1 to 3 carbon atoms, Y represents $-O-$ or $-S-$, and $R_1$ and n are as defined hereinabove.

Use of the mercaptans of formula (V-2) in the reaction of step 2 affords 2-organothio-2-cyclopentenones of formula (I-2). Likewise, use of the mercaptans of formula (V-3) in the reaction of step 2 gives 2-organothio-2-cyclopentenones of the following formula

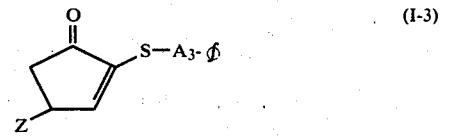

(I-3)

wherein all symbols are as defined hereinabove.

Examples of especially suitable mercaptans are given below.

Mercaptans of formula (V-2)

Alkyl mercaptans such as ethyl mercaptan, n-propyl mercaptan, iso-propyl mercaptan, n-butyl mercaptan, sec-butyl mercaptan, n-pentyl mercaptan, n-hexyl mercaptan, n-octyl mercaptan, n-decyl mercaptan, and n-dodecyl mercaptan; alkenyl mercaptans such as 3-butenyl mercaptan, 3-pentenyl mercaptan, 5-hexenyl mercaptan, and geranyl mercaptan; ω-mercapto fatty acids or esters thereof such as ω-mercaptopropionic acid, ethyl ω-mercaptobutyrate, methyl ω-mercaptocaproate, ω-mercapto-α,α-dimethylcaproic acid, n-hexyl ω-mercaptobutyrate, n-decyl ω-mercaptocaproate, methyl 8-mercaptooct-5-enate, and iso-propyl 8-mercaptooct-5-enate; alkyl mercaptans or alkenyl mercaptans substituted by a hydroxyl group or a protected hydroxyl group, such as β-mercaptoethanol, β-mercapto-α,α-dimethylethanol, 2-hydroxy-2-methyl-n-butyl mercaptan, 2-hydroxy-2-methyl-n-heptyl mercaptan, 2-hydroxy-2-methyl-n-decyl mercaptan, 2-hydroxy-2-methyl-4-heptenyl mercaptan, and 2-hydroxy-2-methyl-5-tetrahydropyranyloxy-n-hexyl mercaptan; and ω-mercapto fatty acids or esters thereof substituted by a hydroxyl group such as 8-hydroxy-8-methyl-9-mercaptononanoic acid, 5-hydroxy-5-methyl-6-mercaptocaproic acid, and methyl 8-hydroxy-8-methyl-9-mercaptononanate.

Mercaptans of formula (V-3)

Aralkyl or cycloalkyl-alkyl mercaptans which are substituted or unsubstituted by one or two trifluoromethyl groups, hydroxy groups or halogen atoms, such as benzyl mercaptan, 3-phenylpropyl mercaptan, 5-phenylpentyl mercaptan, cyclohexylmethyl mercaptan, 2-cyclopentylpropyl mercaptan, m-trifluoromethylbenzyl mercaptan, 2-(p-hydroxyphenyl)ethyl mercaptan, 3-(p-fluorophenyl)propyl mercaptan, and 2-(3,4-dihydroxyphenyl)ethyl mercaptan; mercaptans containing the group —A$_1$—COOR$_1$)$_n$ as a substituent, such as p-tolylmethyl mercaptan, 2-(p-carboxymethylphenyl)ethyl mercaptan, 2-(p-carbomethoxymethylphenyl)ethyl mercaptan, 2-[p-(α-carboxyethyl)phenyl]propyl mercaptan, p-(α-carboxymethoxyethyl)benzyl mercaptan, and 2-(4-carboxymethylcyclohexyl)ethyl mercaptan; and mercaptans containing the group —Y—A$_1$—COOR$_1$)$_n$ as a substituent such as m- or p-(methoxycarbonylmethoxy)benzyl mercaptan, m- or p-(α-carboxyethoxy)benzyl mercaptan, p-methoxybenzyl mercaptan, 3-(p-carboxymethoxyphenyl)propyl mercaptan, 2-[2-(α-carboxyethoxy) cyclopentyl]ethyl mercaptan, and m- or p-(α-carboethoxyethylthio)benzyl mercaptan.

Of these, the ω-mercapto fatty acids or esters thereof, the alkyl mercaptans or alkenyl mercaptans substituted by a hydroxyl group or a protected hydroxyl group, and the phenyl-containing mercaptans having the group—A$_1$—(COOR$_1$)$_n$ or —Y—A$_1$—(COOR$_1$)$_n$ as a substituent are especially preferred.

Thus, use of these mercaptans in the reaction of step 2 affords the corresponding 2-organothio-2-cyclopentenones of formula (I-a) and (I-3) which have especially superior physiological activities.

3. Step 3-1 (synthesis of diorganothiocyclopentanones)

Reaction of the 2-organothio-2-cyclopentenones of formula (I) given hereinabove with mercaptans of the following formula HSR'$_a$ (Va)

wherein R'$_a$ represents a monovalent organic group containing 1 to 25 carbon atoms, and may be identical to or different from R,
in the presence or absence of basic compounds give diorganothiocyclopentanones of the following formula

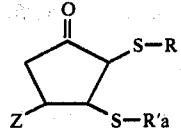
(II'a)

wherein, R, R'$_a$ and Z are as defined hereinabove, (to be referred to as step 3-1-A).

The mercaptans of formula (Va) may be identical to or different from the mercaptans of formula (V).

As needed, the diorganothio-2-cyclopentanone so formed is reduced to a diorganothiocyclopentanol, and if further desired, the hydroxyl group substituted at the cyclopentane ring of the cyclopentanol is converted in a manner known per se to a protected hydroxyl group, thereby forming diorganothiocyclopentanes of the formula

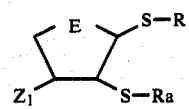
(IIa)

wherein Ra represents a monovalent organic group containing 1 to 25 carbon atoms, and may be identical to or different from R; Z$_1$ represents a hydrogen atom, a hydroxyl group or a protected hydroxyl group, and may be identical to or different from Z; E represents the group >C=O or

in which Z' represents a hydrogen atom, a hydroxyl group, or a protected hydroxyl group; and R is a monovalent organic group containing 1 to 25 carbon atoms, (to be referred to as step 3-1-B).

Accordingly, diorganothiocyclopentanes of the following formula

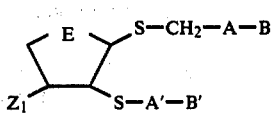
(IIa-1)

wherein Z$_1$ has the same definition as Z, and Z$_1$ may be identical to or different from Z; A, B and E are as defined hereinabove; A' may be different from A in formula (V-1), and represents a divalent or trivalent saturated or unsaturated hydrocarbon group containing 1 to 13 carbon atoms optionally containing a hydroxyl group or a protected hydroxyl group as a substituent; and B' may be identical to B in formula (V-1), and represents an atomic grouping of the formula —(COOR$_1$)$_n$ — (i) in which R$_1$ represents a hydrogen atom or a saturated or unsaturated aliphatic hydrocarbon residue containing 1 to 10 carbon atoms, and n is 0 or 1, with the proviso that when n is 0, —(COOR$_1$)$_n$ represents a hydrogen atom, or an atomic grouping —Y—A$_1$—(COOR$_1$)$_n$—(ii) in which Y is —O— or —S—, A$_1$ represents a divalent saturated or unsaturated aliphatic hydrocarbon group containing 1 to 3 carbon atoms, and R$_1$ and n are as defined with regard to formula (i) above, can be produced by reacting a 2-organothio-2-cyclopentenone of formula (I-1) with a mercaptan of the following formula

wherein A' and B' are as defined above, to form a diorganothiocyclopentanone of the following formula

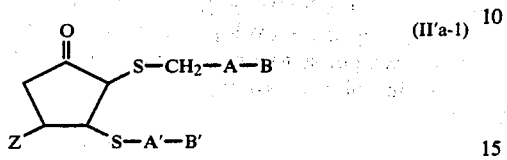

wherein A, B, A', B' and Z are as defined hereinabove, (step 3-1-A); and optionally reducing this compound to a diorganothiocyclopentanol, and further optionally converting the hydroxyl group substituted at its cyclopentane ring to a protected hydroxyl group in a manner known per se (step 3-1-B).

Especially suitable mercaptans within the definition of (V'-1) are those of the following formula

wherein $A'_2$ may be identical to, or different from, $A_2$ in formula V-2, and represents a divalent saturated or unsaturated aliphatic hydrocarbon residue containing 1 to 13 carbon atoms optionally containing a hydroxyl group or a protected hydroxyl group as a substituent; $R'_1$ represents a hydrogen atom, or a saturated or unsaturated aliphatic hydrocarbon group containing 1 to 10 carbon atoms, and may be identical to $R_1$; and m is 0 or 1, and when m is 0, $+COOR'_1)_m$ represents a hydrogen atom. Diorganothiocyclopentanes of the formula

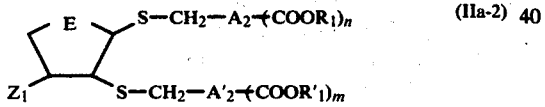

wherein all symbols are as defined above,

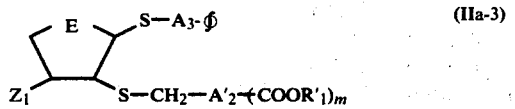

wherein all symbols are as defined above, can be produced by reacting such mercaptans with the 2-organothio-2-cyclopentenones of formula (I-2) or (I-3) above, or optionally reducing the resulting reaction products to diorganothiocyclopentanols, followed, if desired, by converting their hydroxyl group to a protected hydroxyl group.

The diorganothiocyclopentanes of formulae (IIa-2) and (IIa-3) have specific physiological activities and are useful as medicines.

Another embodiment comprises reacting the 2-organothio-2-cyclopentenones of formula (I-2) or (I-3) with mercaptans of the following formula

wherein $A'_3$ and $\phi$ may be identical to or different from $A_3$ and $\phi$ in formula (V-3), and have the same definitions as $A_3$ and, or optionally reducing the resulting products to diorganothiocyclopentanes, and then optionally converting their hydroxyl group to a protected hydroxyl group, thereby to form diorganothiocyclopentanes of the following formula

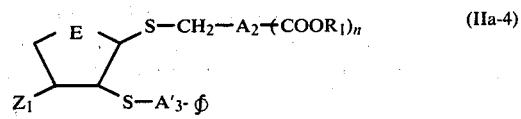

wherein all symbols are as defined in formulae (I-2) and (V'-3),

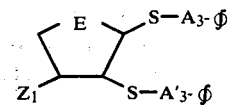

wherein all symbols are as defined in formulae (I-3) and (V'-4).

It should be noted that as can be seen from the formulae (IIa-3) and (IIa-4), some difference in the order of steps is seen between the processes of producing these two kinds of compounds, these formulae may sometimes represent the same compounds.

The reaction of step 3-1-A readily proceeds by merely mixing the 2-organothio-2-cyclopentenone and the mercaptan. Preferably, the reaction is carried out in the presence of a base because it renders the reaction very fast. Piperidine and morpholine are especially suitable bases for this purpose. In order to cause the reaction to proceed smoothly, an inert solvent may be used. Any solvents may be used, and alcohols such as methanol and ethanol, ethers such as diethyl ether and tetrahydrofuran, and hydrocarbons such as hexane and benzene are preferred. The amount of the solvent may be one which is sufficient to cause the reaction to proceed smoothly. Usually, the amount is 1 to 100 times, preferably 2 to 20 times, the volume of the starting materials.

The amount of the mercaptans (Va) used in step 3-1 may be stoichiometrically equimolar to the starting 2-organothiocyclopentenone of formula (I).

The amount of the base which catalyzes the reaction is 0.01 to 20 moles, preferably 0.1 to 2 moles, per mole of the starting materials. Where the mercaptan of formula (Va) contains a carboxyl group, the amount of the base is preferably at least 1 mole per mole of the mercaptan (Va).

The reaction temperature is usually $-20°$ to $100°$ C., preferably $0°$ to $30°$ C.

The resulting product [i.e., the carbonyl compound of formula (IIa')] may, if desired, be subjected to the reduction of the carbonyl group (step 3-1-b). Useful reducing agents for this purpose are those which do not reduce the carbonyl group of the ester of carboxylic acid. Suitable reducing agents include sodium borohydride, lithium trialkyl borohydrides of the formula $LiB(R_d)_3H$ in which $R_d$ is an alkyl group, sodium trialkoxy hydrides of the formula $NaB(OR_c)_3H$ in which $R_c$ is an alkyl group, and lithium aluminum trialkoxy hydrides of the formula $LiAl(OR_e)_3H$ in which $R_e$ is an alkyl group.

The reaction operations in this reduction may be those reported in Fieser and Fieser, Reagents for Organic Syntheses, Vol. 1 to 5 (1967–1975), and J. Org. Chem., 41, 2194 (1976).

Especially preferred species of the mercaptans of formula (Va) used in step 3-1-A are the same as those given hereinabove with regard to the mercaptans (V).

It has been found by the investigations of the present inventors that when a mercaptan containing a carboxyl group or its ester as a substituent is used in step 2, it is not always necessary to use a mercaptan containing a carboxyl group or its ester as a substituent in step 3-1-A, and that the resulting diorganothiocyclopentanes of formula (II) are structurally similar to prostaglandins, i.e., 7,13-dithiaprostanoic acid derivatives which have superior physiological properties. Hence, it has been found that when a mercaptan not containing a carboxyl group or its ester as a substituent is used in step 2, the use of a mercaptan containing a carboxyl group or its ester as a substituent in step 3-1-A is suitable for obtaining preferred diorganothiocyclopentanes, i.e., 7,13-dithiaprostanoic acid derivatives.

4. Step 3-2 (introduction of a hydrocarbon group)

Instead of performing step 3-1, organothiocyclopentanes of the formula

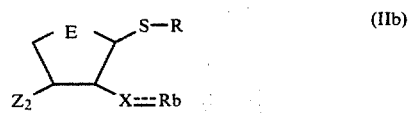
(IIb)

wherein E represents $>C=O$, or

in which Z' represents a hydrogen atom, a hydroxyl group or a protected hydroxyl group; $X_1$ represents $-CH_2-$ or $-CH=$; ==== represents a single or double bond; R is as defined above; Rb represents a monovalent organic group containing 1 to 25 carbon atoms and may be identical to or different from R'b; and $Z_2$ represents a hydrogen atom, a hydroxyl group or a protected hydroxyl group, with the proviso that when E is

and Z' is a hydroxyl group or a protected hydroxyl group, $Z_2$ represents a hydrogen atom,
may be obtained by step 3-2 which comprises reacting a 2-organothio-2-cyclopentenone of the formula

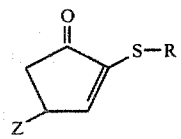
(I)

wherein R and Z are as defined above, with an organocopper lithium compound of the formula

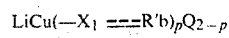
(VI)

wherein all symbols are as defined hereinabove, to form an organothiocyclopentanone of the formula

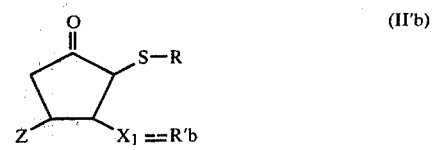
(II'b)

wherein all symbols are as defined hereinabove, (step 3-2-A); and where Z is a hydrogen atom, optionally reducing the resulting compound to an organothiodicyclopentanol, and if further desired, converting its hydroxyl group to a protected hydroxyl group in a manner known per se (step 3-2-B).

Preferred species of the organocopper lithium compounds of formula (VI) used in step 3-2-A are those expressed by the following formula $$LiCu+G-D']_pQ_{2-p} \quad (VI-1)$$

wherein Q and p are as defined in formula (VI); G represents $-CH_2CH_2-$ or $-CH=CH-$; and D' represents a saturated or unsaturated hydrocarbon group containing 1 to 20 carbon atoms which optionally contains one or two trifluoromethyl groups, group of the formula $-OR_3-$(iii) in which $R_3$ represents a tri(lower alkyl)silyl group or a saturated or unsaturated hydrocarbon group containing 1 to 8 carbon atoms optionally containing an ethereal oxygen atom, or groups of the formula

(iv)

in which $R_4$ represents an aliphatic hydrocarbon group containing 2 or 3 carbon atoms, $R_3$ or $R_4$ optionally containing a trifluoromethyl group as a substituent.

Organothiocyclopentanes of the formula

(IIb-1)

wherein all symbols are as defined hereinabove.

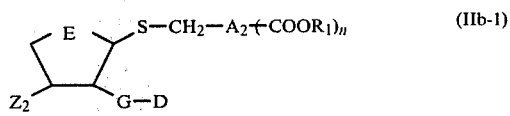
(IIb-2)

wherein all symbols are as defined hereinabove, can be prepared by step 3-2 which comprises reacting the above organocopper lithium compounds with 2-organothiocyclopentenones of the formula

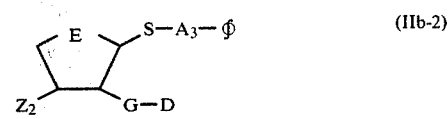
(I-2)

wherein all symbols are as defined hereinabove, or

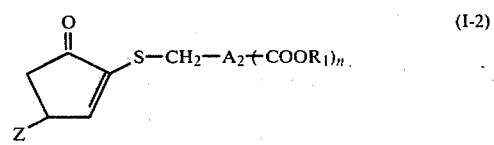

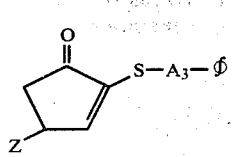

(I-3)

wherein all symbols are as defined hereinabove, (step 3-2-A); and where Z is a hydrogen atom, optionally reducing the resulting reaction products to organothiocyclopentanols, and then optionally converting at least that hydroxyl group which is substituted at their cyclopentane ring to a protected hydroxyl group (step 3-2-B).

The organothiocyclopentanes expressed by formulae (IIb-1) and (IIb-2) are also novel compounds, and because of their specific physiological activities, are useful as medicines.

The organocopper lithium compounds of formula (VI) used in step 3-2-A can be prepared, for example, by reacting organolithium compounds with cuprous salts [see, for example, G. H. Posner, Organic Reactions, Vol. 19, 1 (1972)].

In formula (VI), preferred species of Q include, for example, halogen atoms and such as chlorine, bromine and iodine atoms; alkoxy groups such as a t-butoxy group, aryloxy groups such as a phenoxy group, arylthio groups such as a phenylthio group, dialkylamino groups such as a dimethylamino group, substituted ethynyl groups such as a 1-pentynyl group, and a cyano group.

The organocopper lithium compounds of formula (VI) may also be used in the form of complexes with trivalent phosphorus compounds, such as trialkyl phosphines (e.g., triethyl phosphine, or tri-n-butyl phosphine), trialkyl phosphites (e.g., trimethyl phosphite, triethyl phosphite, triisopropyl phosphite, or tri-n-butyl phosphite), hexamethylphosphorous triamide, or triphenyl phosphine. The use of such complexes frequently tends to increase the yield of the final product.

The process of step 3-2 is performed by reacting the 2-organothio-2-cyclopentenone derivatives with the organocopper lithium compounds of formula (VI) in the presence of aprotic inert organic solvents.

The 2-organothio-2-cyclopentenone derivatives and the organocopper lithium compounds react in stoichiometrically equimolar amounts. Usually, it is preferred that 0.5 to 5.0 moles, preferably 0.8 to 2.0 moles, of the organocopper lithium compounds are reacted with 1 mole of the 2-organothio-2-cyclopentenone derivatives.

The reaction temperature suitable for use in the above reaction is −100° C. to 50° C., preferably −78° C. to 0° C. The reaction time varies according to the reaction temperature. Usually, it is sufficient that the reaction is performed for about 1 hour at a temperature of −78° C. to −20° C.

The reaction is carried out in the presence of aprotic organic solvents which are liquid at the reaction temperature and do not react with the reactants. Examples of suitable aprotic inert organic solvents include saturated hydrocarbons such as pentane, hexane, heptane or cyclohexane, aromatic hydrocarbons such as benzene, toluene or xylene, ethers such as diethyl ether, tetrahydrofuran, dioxane, dimethoxyethane or diethylene glycol dimethyl ether, and aprotic polar solvents such as hexamethylphosphoric triamide (HMP), N,N-dimethylformamide (DMF), N,N-dimethylacetamide (DMAC), dimethylsulfoxide, sulfolane, or N-methylpyrrolidone. These solvents can be used either alone or in admixture of two or more.

The inert organic solvent used in the preparation of the organocopper lithium compound can be directly used in the above reaction. In other words, the reaction may be carried out by adding the 2-organothio-2-cyclopentenone derivative to the reaction system where the organocopper lithium compound has been produced.

The amount of the organic solvent may be one sufficient to cause the reaction to proceed smoothly. Usually, the amount is 1 to 100 times, preferably 2 to 20 times, the volume of the starting materials.

After the reaction, the reaction product of formula (II'b) is separated and purified from the reaction mixture by conventional means such as extraction, washing, chromatography, or combinations of these.

Where Z represents a hydrogen atom, the organothiocyclopentanone derivative of formula (II'b) is optionally reduced to an organothiocyclopentanol, and at least that hydroxyl group which is substituted at its cyclopentane ring is optionally converted to a protected hydroxyl group in a manner known per se, thereby to produce the organothiocyclopentane of formula (IIb) (step 3-2-B). The reducing reaction in step 3-2-B, and the reaction of converting the hydroxyl group to a protected hydroxyl group in step 3-1-B can be performed under the same conditions as set forth hereinabove with regard to step 3-1-B.

The organothiocyclopentanes of formula (IIb) so formed can be separated and recovered from the reaction mixture in the same way as set forth hereinabove with regard to the product of formula (IIa).

Preferred species of the organocopper lithium compounds of formula (VI-1) are shown below.

In formula (VI-1), G is —CH$_2$CH$_2$— or —CH=CH—.

Preferred species of the saturated or unsaturated hydrocarbon groups containing 1 to 20 as represented by D' include methyl, ethyl, propyl, butyl, hexyl, heptyl, octyl, nonyl, decyl, dodecyl, propenyl, butenyl, geranyl, hexenyl, propynyl, 1-ethynylhexyl, 1-methylhexyl, β-phenethyl, γ-phenylpropyl, 3,6-ethanohexyl, and 3,6-methanohexyl.

Preferred species of the substituents of the hydrocarbon group include those of formula (iii) —OR$_3$, such as t-butyldimethylsiloxy, tribenzylsiloxy, trimethylsiloxy, methoxy, t-butoxy, m-trifluoromethylphenoxy, tetrapyranyloxy, and α-ethoxyethyl; and those of formula (iv), in which the two bonds of oxygen are attached to the same carbon atom or two adjacent carbon atoms on the carbon chain or D', such as 1,2-ethylenedioxy, 1,2-propylenedioxy, and isopropylidenedioxy.

Where the 2-organothio-2-cyclopentenones of formula (I) and the organothiocyclopentanes of formula (IIa) and (IIb) contain a free carboxyl group at the side chain of the cyclopentenone or cyclopentane ring, they can be converted to non-toxic salts by reaction with pharmaceutically acceptable inorganic or organic bases.

These non-toxic salts are frequently a preferred form for drug formulation since in oral administration, they become free acids in the stomach and exhibit their pharmacological effects.

The 2-organothio-2-cyclopentenones of formula (I), the organothiocyclopentanes of formulae (IIa) and (IIb), and the salts thereof have various valuable pharmacological activities such as gastric secretion inhibiting action, anti-inflammatory action, platelet aggregation inhibiting action, lipid decomposition inhibiting action, hypotensive action, vasodilating action, broncho-dilating or -constricting action, and diuretic action. Moreover, they have certain actions which affect corpus luteum, ovular transportation in the fallopian tube, implantation, and fertilizing function.

Thus, the compounds of the invention expressed by formulae (I), (IIa) and (IIb) can be used as medicines for humans and animals in admixture with solid, liquid or semi-liquid pharmaceutical vehicles. The vehicles or carriers are non-reactive organic or inorganic compounds nontoxic to humans and animals which are suitable for peroral, parenteral, intrarectal, intraperitoneal, or topical administrations. Such vehicles or carriers have heretofore been widely known in drug manufacture.

Pharmaceutical compositions containing the aforesaid compounds of the invention may, if desired, be sterilized, and further admixed with adjuvants such as lubricants, wetting agents, emulsifiers, preservatives, osmotic pressure controlling agents, stabilizers, colorants, buffers, flavors, or seasonings.

The following Examples illustrate the present invention specifically.

EXAMPLE 1

(1) Preparation of 4-t-butyldimethylsiloxy-2,3-epoxycyclopentan-1-one of the formula:

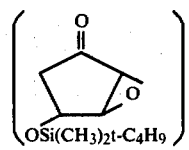

Four hundred (400) milligrams of 4-t-butyldimethylsiloxycyclopent-2-en-1-one was dissolved in 10 ml of methanol, and 5 ml of 35% hydrogen peroxide was added at room temperature. Then, 3 ml of a 2N aqueous solution of sodium hydroxide was added gradually under ice cooling. After the addition, the ice bath was removed, and the mixture was stirred at room temperature for 2 hours. A saturated aqueous solution of ammonium chloride was added, and the mixture was extracted with diethyl ether. The organic layer was washed successively with a saturated aqueous solution of ammonium chloride and a saturated aqueous solution of sodium chloride, and dried over anhydrous magnesium sulfate. The solvent was distilled off, and the resulting oily product was chromatographed on a thin layer plate with cyclohexane/ether (8/2) to afford 345 mg of 4-t-butyldimethylsiloxy-2,3-epoxycyclopentan-b 1-one in a yield of 80%. The spectral data of this product were as follows:

IR (film): 1750, 1260, 905, 830 cm$^{-1}$.

NMR (CCl$_4$, ppm): 0.05 (6H), 0.78 (9H, s), 1.70 (1H, d, J=18 Hz), 2.40 (1H, dd, J=18 and 5 Hz), 3.20 (1H, s), 3.60 (1H, s), 4.48 9 (1H, d, J=5 Hz).

(2) Preparation of 4-t-butyldimethylsiloxy-2-n-octylthiocyclopent-2-en-1-one [designated (1)] of the formula:

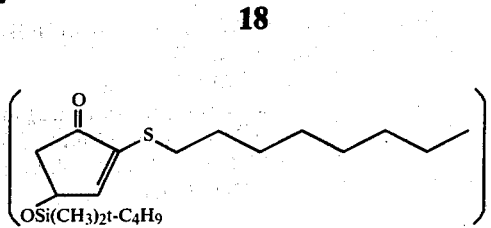

The 4-t-butyldimethylsiloxy-2,3-epoxycyclopentan-1-one obtained above (212 mg) and 146 mg of n-octyl mercaptan were dissolved in 5 ml of diethyl ether, and 148 mg of triethylamine was added. The mixture was stirred at room temperature for 1 hour. The reaction mixture was poured into an aqueous solution of ammonium chloride, and extracted with ethyl acetate. The extract was treated by ordinary methods. The resulting crude product was chromatographed on a thin layer plate with cyclohexane/ethyl acetate (6/4) to afford 110 mg of 4-t-butyldimethylsiloxy-2-n-octylthiocyclopent-2-en-1-one in a yield of 35% which was found to have the following characteristics.

IR (film): 1720 cm$^{-1}$.

NMR (CCl$_4$, ppm): 0.08 (6H, s), 0.9 (9H, s), 0.9 (3H, t), 1.3–1.6 (12H), 2.0–3.1 (4H), 4.1 (1H, m), 6.90 (1H, t).

Mass (70 eV, m/e): 356 (M+).

The following compounds were produced by similarly reacting 4-t-butyldimethylsiloxy-2,3-epoxycyclopentan-1-one with the corresponding mercaptans.

(2) 4-t-Butyldimethylsiloxy-2-n-heptylthiocyclopent-2-en-1-one,
(3) 4-t-butyldimethylsiloxy-2-geranylthiocyclopent-2-en-1-one,
(4) 4-t-butyldimethylsiloxy-2-(2-hydroxy-2-methylheptylthio)cyclopent-2-en-1-one,
(5) 4-t-butyldimethylsiloxy-2-(3-phenylpropyl)cyclopent-2-en-1-one,
(6) 4-t-butyldimethylsiloxy-2-[m- or p-(1-carboxyethoxy)benzylthio]cyclopent-2-en-1-one, and
(7) 4-t-butyldimethylsiloxy-2-[m- or p-(1-carboxyethyl)benzylthio]cyclopent-2-en-1one.

EXAMPLE 2

Preparation of 4-hydroxy-2-n-octylthiocyclopent-2-en-1-one (8) of the formula:

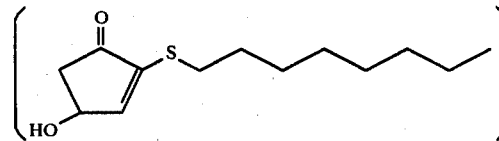

4-t-Butyldimethylsiloxy-2-n-octylthiocyclopent-2-en-1-one (90 mg) was dissolved in 5 ml of a mixture of acetic acid, water and tetrahydrofuran in a ratio of 3:1:1, and reacted at room temperature for 48 hours. The reaction mixture was neutralized with sodium bicarbonate, and extracted with ethyl acetate. The extract was treated by conventional methods, and chromatographed on a thin layer plate with cyclohexane/ethyl acetate (4/6) to afford 48 mg of 4-hydroxy-2-n-octylthiocyclopent-2-en-1-one in a yield of 84% showing a single spot. The resulting product had the following characteristics.

IR (film): 3350, 1720 cm$^{-1}$.

NMR (CCl₄, ppm): 0.9 (3H, t), 1.3–1.6 (12H), 1.7–2.9 (5H), 4.1 (1H, m), 6.9 (1H, d).

Mass (70 eV, m/e): 224 (M⁺ −18).

In a similar manner, hydrolysis of 4-t-butyldimethylsiloxy-2-(alkyl or alkenyl)thiocyclopent-2-en-1-ones afforded the following corresponding 4-hydroxy-2-(alkyl or alkenyl)thiocyclopent-2-en-1-ones.

(9) 4-hydroxy-2-n-heptylthiocyclopent-2-en-1-one,
(10) 4-hydroxy-2-geranylthiocyclopent-2-en-1-one,
(11) 4-hydroxy-2-(2-hydroxy-2-methylheptylthio)cyclopent-2-en-1-one,
(12) 4-hydroxy-2-(3-phenylpropyl)cyclopent-2-en-1-one,
(13) 4-hydroxy-2-[m- or p-(1-carboxyethoxy)benzylthio]cyclopent-2-en-1-one, and
(14) 4-hydroxy-2-[m- or p-(1-carboxyethyl)benzylthio]cyclopent-2-en-1-one.

EXAMPLE 3

Preparation of 4-t-butyldimethylsiloxy-2-(3-carbomethoxypropylthio)cyclopent-2-en-1-one (15) of the formula:

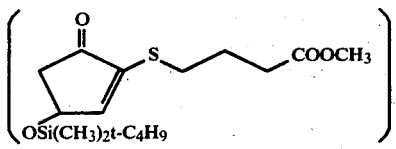

4-t-Butyldimethylsiloxy-2,3-epoxycyclopent-2-en-1-one produced in the same way as in Example 1, (1) (212 mg) and 123 mg of methyl ω-mercaptopropionate were dissolved in methanol, and 95 mg of triethylamine was added. They were reacted at room temperature for 30 minutes. The methanol was distilled off at reduced pressure from the reaction mixture, and diethyl ether and an aqueous solution of ammonium chloride were added. The aqueous layer was extracted with diethyl ether. The extract was treated by customary methods, and the resulting crude product was chromatographed on a thin layer plate with cyclohexane/ethyl acetate (=6/4) to afford 217 mg of 4-t-butyldimethylsiloxy-2-(3-carbomethoxypropylthio)cyclopent-2-en-1-one in a yield of 69%. The product had the following characteristics.

IR (film): 1745, 1715 cm⁻¹.

NMR (CCl₄, ppm): 0.08 (6H), 0.9 (9H), 1.8–3.1 (6H), 3.6 (3H, s), 4.05 (1H, m), 6.90 (1H, t).

Mass (70 eV, m/e): 330 (M⁺).

EXAMPLE 4

Preparation of 2-(3-carbomethoxypropylthio)-4-hydroxy-cyclopent-2-en-1-one (16) of the formula:

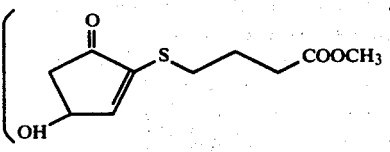

4-t-Butyldimethylsiloxy-2-(3-carbomethoxypropylthio)cyclopent-2-en-1-one (200 mg) was treated and purified in the same way as in Example 2 to afford 110 mg of 2-(3-carbomethoxypropylthio)-4-hydroxycyclopent-2-en-1-one in a yield of 85%. The product had the following characteristics.

IR (film): 1745, 1715 cm⁻¹.

NMR (CCl₄, ppm): 1.8–3.1 (7H), 3.6 (3H, s), 4.05 (1H, m), 6.85 (1H, t).

Mass (70 eV, m/e): 216 (M⁺).

EXAMPLE 5

Preparation of 4-t-butyl-dimethylsiloxy-2-(5-methoxycarbonylpentylthio)cyclopent-2-en-1-one (17) of the formula:

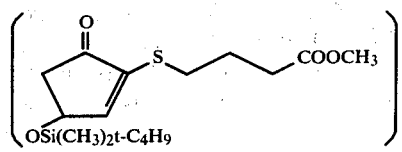

4-t-Butyldimethylsiloxy-2,3-epoxycyclopentan-1-one (1.14 g) was dissolved in 10 ml of methanol, and 910 mg of methyl ω-mercaptocaproate was added, followed by dropwise addition of 500 mg of triethylamine. The mixture was reacted at room temperature for 20 minutes, and then treated and purified in the same way as in Example 3 to afford 1.16 g of 4-t-butyldimethylsiloxy-2-(5-methoxycarbonylpentylthio)cyclopent-2-en-1-one in a yield of 64%. The product had the following characteristics.

IR (film): 1745, 1715, 840, 760 cm⁻¹.

NMR (CCl₄, ppm): 0.68 (6H, s), 0.9 (9H, s), 1.8–3.0 (12H), 3.6 (3H, s), 4.85 (1H, m), 6.65 (1H, d, J=3 Hz).

Mass (70 eV, m/e): 372 (M⁺).

EXAMPLE 6

(1) Preparation of 2,3-epoxy-4-(2-tetrahydropyranyloxy)cyclopentan-1-one of the formula

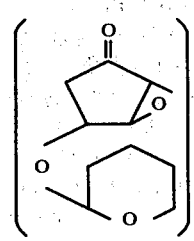

One gram of 4-(2-tetrahydropyranyloxy)cyclopent-2-en-1-one was dissolved in 20 ml of methanol, and 10 ml of 30% hydrogen peroxide was added at room temperature. Then, with ice cooling, 3 ml of a 2 N aqueous solution of sodium hydroxide was added slowly. The mixture was stirred at room temperature for 1.5 hours. The reaction mixture was post-treated in the same way as in Example 1, (1). The resulting crude product was chromatographed on a thin layer plate with cyclohexane/ethyl acetate (=7/3) to afford 730 mg of 2,3-epoxy-4-(2-tetrahydropyranyloxy)cyclopentan-1-one in a yield of 84%. The product had the following spectral data.

IR (film): 1750 cm⁻¹.

NMR (CCl₄, ppm): 1.62 (6H, s), 1.8–2.8 (2H, m), 3.2–4.1 (4H, m), 4.35–4.85 (2H, m).

(2) Preparation of 2-n-heptylthio-4-tetrahydropyranyloxycyclopent-2-en-1-one (18) of the formula:

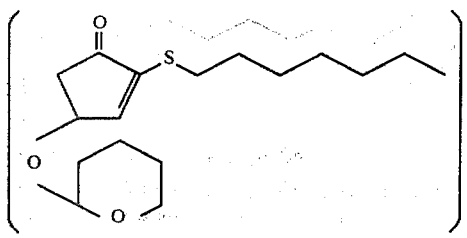

2,3-Epoxy-4-tetrahydropyranyloxycyclopentan-1-one (200 mg) and 121 mg of n-heptylmercaptan were dissolved in 5 ml of methanol, and 158 mg of triethylamine was added. The mixture was stirred at room temperature for 2 hours. The reaction mixture was poured into an aqueous solution of ammonium chloride, and extracted with ethyl acetate. The extract was treated by a customary procedure to afford 280 mg of a crude product. The crude product was chromatographed on a thin layer plate with cyclohexane/ethyl acetate (=6/4) to afford 80 mg of 2-n-heptylthio-4-tetrahydropyranyloxycyclopent-2-en-1-one in a yield of 26%. The product had the following characteristics.

IR (film): 1720 cm$^{-1}$.
NMR (CCl$_4$, ppm): 0.9 (3H, t), 1.3–1.6 (14H), 2.3–3.1 (4H, m), 3.2–4.0 (2H), 4.73 (2H, bs), 6.80 (1H, t).
Mass (70 eV, m/e): 312 (M$^+$).

Similarly, 2,3-epoxy-4-tetrahydropyranyloxycyclopentan-1-one was reacted with mercaptans to afford the following corresponding compounds.

(19) 2-n-Octylthio-4-4-tetrahydropyranyloxycyclopent-2-en-1-one,
(20) 2-geranylthio-4-tetrahydropyranyloxycyclopent-2-en-1-one,
(21) 2-(2-hydroxy-2-methylheptylthio)-4-tetrahydropyranyloxycyclopent-2-en-1-one, and
(22) 2-(3-phenylpropylthio)-4-tetrahydropyranyloxycyclopent-2-en-1-one.

EXAMPLE 7

Preparation of 2-n-heptylthio-4-hydroxycyclopent-2-en-1-one (23) of the formula:

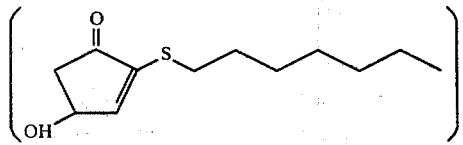

2-n-Heptylthio-4-tetrahydropyranyloxycyclopent-2-en-1-one (80 mg) was dissolved in 5 ml of a mixture of acetic acid, water and tetrahydrofuran in a ratio of 3:1:1 and 2 ml of acetic acid, and the solution was allowed to stand at room temperature for 12 hours. The reaction mixture was neutralized with sodium bicarbonate, and extracted with ethyl acetate. The extract was treated by a customary procedure to afford 58 mg (95% yield) of 2-n-heptylthio-4-hydroxycyclopent-2-en-1-one having a single spot in thin-layer chromatography (cyclohexane/ethyl acetate=4/6). The product had the following characteristics.

IR (film): 3350, 1720 cm$^{-1}$.
NMR (CCl$_4$, ppm): 0.9 (3H, t), 1.3–1.6 (10H), 1.7–2.9 (5H), 1.4 (1H, m), 6.9 (1H, d).

Mass (70 eV, m/e): 210 (M$^+$ −18).

EXAMPLE 8

Preparation of 2-(5-carbomethoxypentylthio)-4-tetrahydropyranyloxycyclopent-2-en-1-one (24) of the formula:

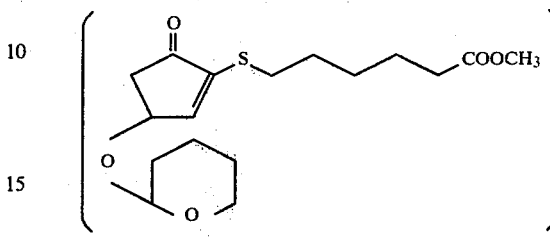

2,3-Epoxy-4-tetrahydropyranyloxycyclopentan-1-one (270 mg) and 226 mg of methyl ω-mercaptocaproate were dissolved in 4 ml of methanol, and 141 mg of triethylamine was added. The mixture was reacted at room temperature for 2 hours. The reaction mixture was post-treated in the same way as in Example 3 to afford 485 mg of a crude product. The crude product was chromatographed on a thin layer plate with cyclohexane/ethyl acetate (=6/4) to afford 2-(5-carbomethoxypentylthio)-4-tetrahydropyranyloxycyclopent-2-en-1-one which was found to have the following characteristics.

Melting point: 41°–42° C.
IR (film): 1745, 1720, 1040 cm$^{-1}$.
NMR (CCl$_4$, ppm): 1.6 (2H), 2.3–3.2 (6H), 3.6 (3H, s), 3.6–4.1 (2H), 4.8 (2H), 6.9 (1H, t).
Mass (70 eV, m/e): 342 (M$^+$).

Reaction of 2,3-epoxy-4-tetrahydropyranyloxycyclopentan-1-one with mercaptans in a similar manner afforded the following corresponding compounds.

(25) 2-(2-Carbomethoxyethylthio)-4-tetrahydropyranyloxycyclopent-2-en-1-one,
(26) 2-(5-carboethoxy-5,5-dimethylpentylthio)-4-tetrahydropyranyloxycyclopent-2-en-1-one,
(27) 2-(5-carbomethoxy-4-pentenylthio)-4-tetrahydropyranyloxycyclopent-2-en-1-one,
(28) 2-[m- or p-(α-carboxyethyl)benzylthio]-4-tetrahydropyranyloxycyclopent-2-en-1-one, and
(29) 2-[m- or p-(α-carboxyethoxy)benzylthio]-4-tetrahydropyranyloxycyclopent-2-en-1-one.

EXAMPLE 9

Production of 2-(5-carbomethoxypentylthio)-4-hydroxycyclopent-2-en-1-one (30) of the formula:

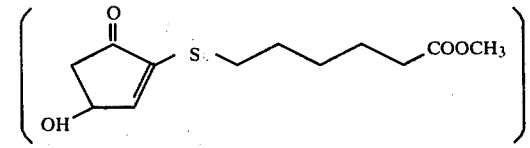

Purified 2-(5-carbomethoxypentylthio)-4-tetrahydropyranyloxycyclopent-2-en-1-one (480 mg) was dissolved in 10 ml of a mixture of acetic acid, water and tetrahydrofuran in a ratio of 3:1:1, and 3 ml of acetic acid was further added. The mixture was worked up at room temperature for 12 hours. The reaction mixture was post-treated in the same way as in Example 6, (2) to afford 450 mg of a crude product. The crude product was chromatographed on a thin layer plate with cyclohexene/ethyl acetate (=6/4) to afford 180 mg of 2-(5-carbomethoxypentylthio)-4-hydroxycyclopent-2-en-1-one in a yield of 50%. The product had the following characteristics.

IR (film): 3400, 1740, 1715 cm$^{-1}$.

NMR (CDCl$_3$, ppm): 1.5 (6H), 2.1–3.2 (7H), 3.6 (3H, s), 4.9 (1H, q), 6.9 (1H, d).

Mass (70 eV, m/e): 258 (M+), 240 (M+ −18).

EXAMPLE 10

Preparation of 2-(5-carboxypentylthio)-4-hydroxycyclopent-2-en-1-one (31) of the formula:

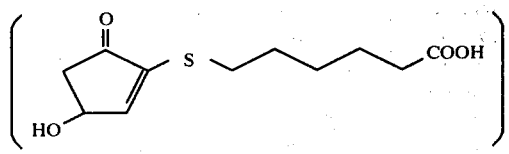

Purified 2-(5-carbomethoxypentylthio)-4-tetrahydropyranyloxycyclopent-2-en-1-one (340 mg) was reacted in 1 ml of a 1 N aqueous solution of sodium hydroxide and 5 ml of methanol at room temperature for 2 hours. After the reaction, the reaction mixture was acidified with dilute hydrochloric acid, and allowed to stand for 6 hours, after which it was extracted with ethyl acetate. The extract was treated in a customary manner to afford 220 mg of a crude product. The crude product was chromatographed on a thin layer plate with cyclohexane/ethyl acetate/acetic acid (=60/40/3) to afford 120 mg of 2-(5-carboxypentylthio)-4-hydroxycyclopent-2-en-1-one in a yield of 49%. The product had the following characteristics.

IR (film): 3400, 1720 cm$^{-1}$.

NMR (CDCl$_3$, ppm): 1.5 (6H), 2.1–3.2 (6H), 4.9 (1H, m), 6.85 (1H, bs), 9.8 (2H, bs).

Mass (12 eV, m/e): 226 (M+ −18).

Solvolysis of 2-(carboxy- or alkoxycarbonyl-substituted organothio)-4-tetrahydropyranyloxycyclopent-2-en-1-ones in a similar manner afforded the following corresponding 2-(carboxy-substituted organothio)-4-hydroxycyclopent-2-en-1-ones.

(32) 2-(2-Carboxyethylthio)-4-hydroxycyclopent-2-en-one,
(33) 2-(5-carboxy-5,5-dimethylpentylthio)-4-hydroxycyclopent-2-en-1-one,
(34) 2-(5-carboxy-4-pentenylthio)-4-hydroxycyclopent-2-en-1-one,
(35) 2-[m- or p-(α-carboxyethyl)benzylthio]-4-hydroxycyclopent-2-en-1-one, and
(36) 2-[m- or p-(α-carboxyethoxy)benzylthio]-4-hydroxycyclopent-2-en-1-one.

EXAMPLE 11

Preparation of 2-n-heptylthiocyclopent-2-en-1-one (37) of the formula:

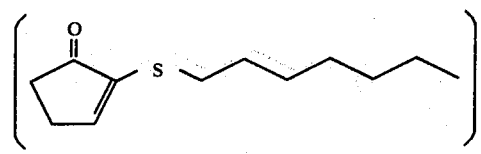

Cyclopentenone (3.40 g) was oxidized in 15 ml of methanol using 4.4 ml of an aqueous solution of hydrogen peroxide and 4 ml of a 3 N aqueous solution of sodium hydroxide to afford crude 2,3-epoxycyclopentanone. To the crude product was added dropwise slowly 30 ml of a solution of 3.20 g of n-heptylmercaptan in methanol at room temperature over the course of 1.5 hours. Thirty minutes after the end of addition, the reaction mixture was concentrated under reduced pressure, and diethyl ether was added. The organic layer was washed with water, and treated in a customary manner to afford 5.21 g of a crude product. The crude product was chromatographed with cyclohexane/ethyl acetate (=8/2) to afford 2.50 g of 2-n-heptylthiocyclopent-2-en-1-one in a yield of 49%. The product had the following characteristics.

IR (film): 1705, 1575 cm$^{-1}$.

NMR (CCl$_4$, ppm): 0.9 (3H, t), 1.3 (10H), 2.1–2.9 (6H), 7.05 (1H, dd).

Mass (70 e/V, m/e): 212 (M+).

Similarly, 2,3-epoxycyclopentanone was reacted with mercaptans to afford the following corresponding compounds.

(38) 2-n-Propylthiocyclopent-2-en-1-one,
(39) 2-geranylthiocyclopent-2-en-1-one,
(40) 2-n-butylthiocyclopent-2-en-1-one,
(41) 2-(5-5-hexenylthio)cyclopent-2-en-1-one, and
(42) 2-n-dodecylcyclopent-2-en-1-one.

EXAMPLE 12

Preparation of 2-n-octylthiocyclopent-2-en-1-one (43) of the formula:

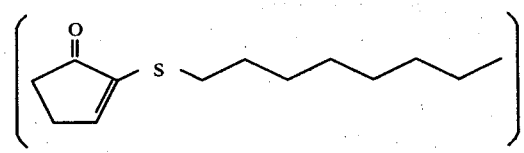

The procedure of Example 11 was repeated except that 3.50 g of n-octylmercaptan was used instead of 3.20 g of n-heptylmercaptan. The crude product was chromatographed under the same conditions to afford 2.90 g of 2-n-octylthiocyclopent-2-en-1-one in a yield of 53%. The product had the following characteristics.

IR (film): 1710 cm$^{-1}$.

NMR (CCl$_4$, ppm): 0.9 (3H, t), 1.3 (12H), 2.1–2.9 (6H), 7.00 (1H, dd).

Mass (70 eV, m/e): 226 (M+).

Similarly, the following compounds were prepared.

(44) 2-Cyclohexylmethylthiocyclopent-2-en-1-one, and
(45) 2-(2-cyclopentylethylthio)cyclopent-2-en-1-one.

EXAMPLE 13

Preparation of 2-(3-phenylpropylthio)cyclopent-2-en-1-one (46) of the formula:

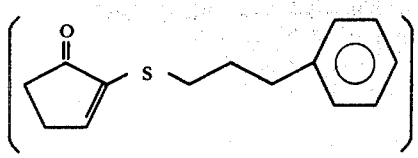

2,3-Epoxycyclopentanone (1.0 g) and 1.06 g of 3-phenylpropyl mercaptan were dissolved in 20 ml of diethyl ether, and 20 drops of triethylamine were added. They were reacted at room temperature for 2 hours. After the reaction, the solvent was distilled off from the reaction mixture under reduced pressure. The residue (1.50 g) was chromatographed on a dry column with cyclohexane/ethyl acetate (=8/2) to afford 1.03 g of 2-(3-phenylpropylthio)cyclopent-2-en-1-one in a yield of 64%. The product had the following characteristics.

IR (film): 3030, 1715, 950, 785, 750, 690 cm$^{-1}$.

NMR (CCl$_4$, ppm): 1.95 (2H, dt, J=7 Hz), 2.2–3.0 (8H, m), 6.95 (1H, t, J=3 Hz), 7.13 (5H, s).

Mass (70 eV, m/e): 232 (M+).

Similarly, 2,3-epoxycyclopentanone was reacted with mercaptans to afford the following corresponding compounds.

(47) 2-Benzylthiocyclopent-2-en-1-one,
(48) 2-(5-phenylpentylthio)cyclopent-2-en-1-one,
(49) 2-[2-(p-hydroxyphenyl)ethylthio]cyclopent-2-en-1-one,
(50) 2-(m-trifluoromethylbenzylthio)cyclopent-2-en-1-one,
(51) 2-[3-(p-fluorophenyl)propylthio]cyclopent-2-en-1-one,
(52) 2-(p-methylbenzylthio-cyclopent-2-en-1-one, and
(53) 2-(p-methoxybenzylthio)cyclopent-2-en-1-one.

EXAMPLE 14

Preparation of 2-(2-hydroxy-2-methylheptylthio)cyclopent-2-en-1-one (54) of the formula:

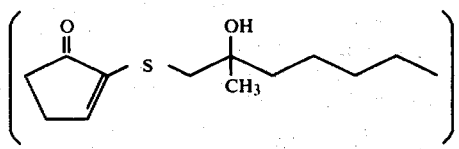

2,3-Epoxycyclopentanone (1.47 g) and 2.0 g of 2-hydroxy-2-methylheptyl mercaptan were dissolved in 30 ml of diethyl ether, and 30 drops of triethylamine were added. They were reacted at room temperature for 2 hours. The solvent was distilled off from the reaction mixture to afford 4.01 g of a crude product. The crude product was chromatographed on a dry column with cyclohexane/ethyl acetate (=8/2) to afford 2.07 g of 2-(2-hydroxy-2-methylheptylthio)cyclopent-2-en-1-one in a yield of 69%. The product had the following characteristics.

IR (film): 3450, 1715, 960, 790 cm$^{-1}$.

NMR (CCl$_4$, ppm): 0.9 (3H, t, J=7 Hz), 1.19 (3H, s), 1.0–1.8 (8H), 2.2–2.8 (5H), 2.85 (2H, s), 7.20 (1H, t, J=3 Hz).

Mass (12 eV, m/e): 242 (M+), 224 (M+—H$_2$O).

Similarly, 2,3-epoxycyclopentanone was reacted with mercaptans to afford the following corresponding compounds.

(55) 2-(2-Hydroxyethylthio)cyclopent-2-en-1-one,
(56) 2-(2-hydroxy-2-methyl-n-butylthio)cyclopent-2-en-1-one,
(57) 2-(2-hydroxy-2-methyl-n-decylthio)cyclopent-2-en-1-one,
(58) 2-[2-hydroxy-2-(p-fluorophenoxy)propylthio]cyclopent-2-en-1-one,
(59) 2-[2-hydroxy-2-(p-fluorophenyl)propylthio]cyclopent-2-en-1-one, and
(60) 2-(2-hydroxy-2-methyl-4-heptenylthio)cyclopent-2-en-1-one.

EXAMPLE 15

Preparation of 2-(5-carbomethoxypentylthio)cyclopent-2-en-1-one (61) of the formula:

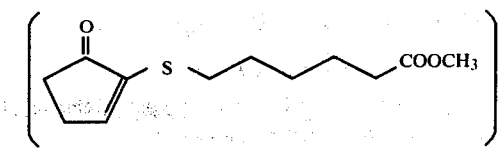

2,3-Epoxycyclopentanone (1.0 g) and 0.65 g of methyl ω-mercaptocaproate were dissolved in 6 ml of methanol, 512 mg of triethylamine was added. They were reacted at room temperature for 30 minutes. The methanol was distilled off from the reaction mixture under reduced pressure, and diethyl ether and an aqueous solution of ammonium chloride were added. The aqueous layer was extracted with diethyl ether to afford 1.70 g of a crude product. The crude product was chromatographed on a thin layer plate with cyclohexane/ethyl acetate (=6/4) to afford 740 mg of 2-(5-carbomethoxypentylthio)cyclopent-2-en-1-one in a yield of 78%. The product had the following characteristics.

Melting point: 45°–46.5° C.

IR (nujol): 1745, 1720 cm$^{-1}$.

NMR (CCl$_4$, ppm): 1.6 (6H), 2.1–3.0 (3H), 3.6 (3H, s), 7.1 (1H, t).

Mass (70 eV, m/e): 242 (M+).

Similarly, 2,3-epoxycyclopentanone was reacted with mercaptans to afford the following corresponding compounds.

(62) 2-(5-Carbodecyloxypentylthio)cyclopent-2-en-1-one,
(63) 2-(2-carbomethoxyethylthio)cyclopent-2-en-1-one,
(64) 2-(3-carboethoxypropylthio)cyclopent-2-en-1-one,
(65) 2-(7-carbomethoxy-3-octenylthio-cyclopent-2-en-1-one, and
(66) 2-(2hydroxy-2-methyl-8-carbomethoxyoctylthio)-cyclopent-2-en-1-one.

EXAMPLE 16

Preparation of 2-(5-carboxypentylthio)cyclopent-2-en-1-one (67) of the formula:

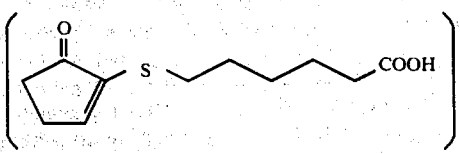

2-(5-Carbomethoxypentylthio)cyclopent-2-en-1-one (133 mg) was treated with 0.8 ml of a 3 N aqueous solution of sodium hydroxide in 5 ml of methanol and 2 ml of water at room temperature for 45 minutes. After the reaction, the reaction mixture was extracted with diethyl ether. The aqueous layer was acidified with hydrochloric acid, and extracted with diethyl ether. The extracts were treated in a customary manner to afford 125 mg of a crude product. The crude product was chromatographed on a thin layer plate with diethyl ether/isopropyl ether/acetic acid (=75/30/3) to afford 65 mg of 2-(5-carboxypentylthio)cyclopent-2-en-1-one in a yield of 49%. The product had the following characteristics.

Melting point: 77.5–78° C.
IR (CCl4): 1720, 1710 cm$^{-1}$.
NMR (CCl4, ppm): 1.6 (6H), 2.1–2.9 (8H), 7.1 (1H, t), 10.2 (1H, bs).
Mass (70 eV, m/e): 210 (M+ − 18).

EXAMPLE 17

Preparation of 2-(3-carbomethoxypropylthio)cyclopent-2-en-1-one (68) of the formula:

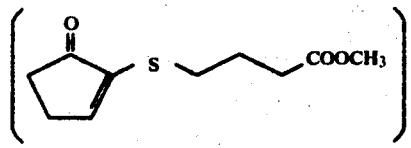

2,3-Epoxycyclopentanone (6.8 g) and 0.45 g of methyl ω-mercaptopropionate were dissolved in 5 ml of ethanol, and 300 mg of triethylamine was added. The mixture was treated and purified in the same way as in Example 15 to afford 440 mg of 2-(3-carbomethoxypropylthio)cyclopent-2-en-1-one in a yield of 55%. The product had the following characteristics.

IR (film): 1745, 1715 cm$^{-1}$.
NMR (CCl4, ppm): 1.8–3.1 (8H), 3.6 (3H, s), 7.0 (1H, t).
Mass (70 eV, m/e): 200 (M+).

EXAMPLE 18

Preparation of 2-[m-(1-carboxyethoxy)benzylthio]-2-cyclopent-2-en-1-one (68) of the formula:

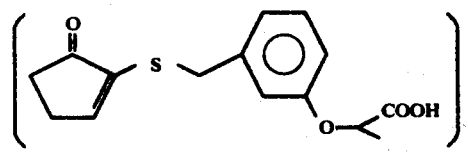

To 196 mg (2.0 millimoles) of 2,3-epoxycyclopentanone produced in the same way as in Example 11 was added 5 ml of a solution of 424 mg (2.0 millimoles) of 2-(m-mercaptomethylphenoxy)propionic acid in methanol. Then, 348 mg (3.4 millimoles) of triethylamine was added dropwise at 0° C. Then, the mixture was stirred at room temperature for about 1 hour. The reaction mixture was treated in a customary manner and extracted with ethyl acetate to afford 478 mg of a crude product. The crude product was chromatographed on a thin layer plate with isopropyl ether/diethyl ether/acetic acid (=80/20/3) to afford 187 mg of 2-[m-(1-carboxyethy)benzylthio]-2-cyclopent-2-en-1-one in a yield of 32%. The product had the following characteristics.

IR (nujol): 1730, 1700 cm$^{-1}$.
NMR (CDCl3, ppm): 1.65 (3H, d), 2.27–2.78 (4H, m), 4.00 (2H, s), 4.78 (1H, q), 6.50–7.36 (5H, m), 8.95 (1H, bs).
Mass (70 eV, m/e): 292 (M+).

Similarly, 2,3-epoxycyclopentanone was reacted with mercaptans to afford the following corresponding compounds.

(70) 2-(m-Carboxymethylbenzylthio)cyclopent-2-en-1-one,
(71) 2-[(2-m-carboxymethylphenyl)ethylthio]cyclopent-2-en-1-one,
(72) 2-[m-(1-carboxyethyl)benzylthio]cyclopent-2-en-1-one,
(73) 2-[2-{m-(1-carboxyethyl)phenyl}propylthio]cyclopent-2-en-1-one,
(74) 2-[m-(carbomethoxymethoxy)benzylthio]cyclopent-2-en-1-one, and
(75) 2-[2-(4-carboxymethylcyclohexyl)ethylthio]cyclopent-2-en-1-one.

EXAMPLE 19

Preparation of 2-[p-(1-carboxyethoxy)benzylthio]-2-cyclopent-2-en-1-one (76) of the formula:

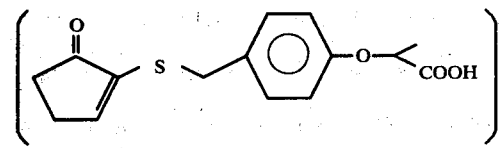

2,3-Epoxycyclopentanone (311 mg; 3.2 millimoles) prepared in the same way as in Example 11 was dissolved in 2 ml of methanol, and 3 ml of a methanol solution of 628 mg (3.0 millimoles) of 2-(p-mercaptomethylphenoxy)propionic acid was added. Further, 450 mg (4.5 millimoles) of triethylamine was added dropwise at 0° C., and the mixture was stirred at room temperature for about 70 minutes. The reaction mixture was worked up in a customary manner to afford 755 mg of a crude product. The crude product was purified in the same way as in Example 18 to afford 297 mg of 2-[p-(1-carboxyethoxy)benzylthio]-2-cyclopent-2-en-one in a yield of 34%. The product had the following characteristics.

IR (nujol): 1730, 1700 cm$^{-1}$.
NMR (CDCl3, ppm): 1.60 (3H, d), 2.28–2.77 (4H, m), 3.96 (2H, s), 4.75 (1H, q), 6.45–7.38 (5H, m), 9.3 (1H, bs).
Mass (70 eV, m/e): 292 (M+).

Similarly, 2,3-epoxycyclopentanone was reacted with mercaptans to afford the following corresponding compounds.

(77) 2-(p-Carboxymethylbenzylthio)cyclopent-2-en-1-one,
(78) 2-[2-(p-carboxymethylphenyl)ethylthio]cyclopent-2-en-1-one,
(79) 2-[p-(1-carboxyethyl)benzylthio]cyclopent-2-en-1-one,
(80) 2-[2-{p-(1-carboxyethyl)phenyl}propylthio]cyclopent-2-en-1-one,
(81) 2-[p-(carbomethoxymethyl)benzylthio]cyclopent-2-en-1-one, and

(82) 2-[2-(4-carboxymethylcyclohexyl)ethylthio]cyclopent-2-en-1-one.

EXAMPLE 20

Preparation of 11-deoxy-7-thia-prostaglandin $E_1$ methyl ester, t-butyldimethylsilyl ether (83) of the formula:

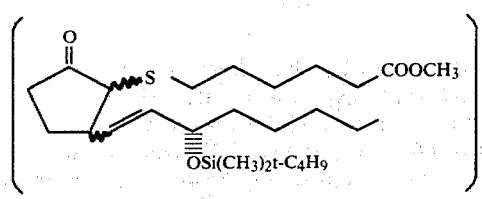

3(S)-t-Butyldimethylsiloxy-1-iodo-oct-1-ene (1.10 g) was dissolved in 8 ml of diethyl ether, and 4.5 ml of t-butyl lithium (as a 1.4 M pentane solution) was added at −78° C. The mixture was stirred for 2 hours. Then, a solution of a copper complex prepared from 482 mg of hexamethylphosphoric triamide (HMP) and 5 ml of diethyl ether was added dropwise, and the reaction was performed at −78° C. for 1 hours. To the resulting lithium organocuprate solution was added slowly over the course of 10 minutes at −78° C. a diethyl ether solution (5 ml) of 480 mg of 2-(ω-carbomethoxypentylthio)cyclopent-2-en-1-one. The mixture was stirred for 1 hour, and the reaction temperature was raised to −20° C. The reaction was stopped by addition of a saturated aqueous solution of ammonium chloride, and the reaction mixture was extracted three times with 20 ml of hexane. The extract was treated in a customary manner to afford 1.40 g of a crude product. The crude product was chromatographed on a dry column with hexane/ethyl acetate (=8/2) to afford 153 mg of a diastereomeric mixture of t-butyldimethyl silyl ether of 11-deoxy-7-thia-prostaglandin $E_1$ methyl ester (to be referred to as 11-deoxy-7-thia-PGE$_1$ methyl ester) and its 8,12-diepi-isomer in a yield of 12%. The product had the following characteristics.

IR (film): 2940, 1740, 1255, 840, 778 cm$^{-1}$.
NMR (CCl$_4$, ppm): 0.08 (6H, s), 0.9 (12H, bs), 1.2–2.0 (14H), 2.0–2.9 (9H), 3.1 (1H), 3.6 (3H, s), 4.05 (1H, m), 5.55 (2H, m).
Mass (70 eV, m/e): 484 (M$^+$).

Similarly, the following compounds were prepared.

(84) 11-Deoxy-7-thia-ω-homoprostaglandin $E_1$ methyl ester, t-butyldimethylsilyl ether, and its 8-12-diepi-isomer.
(85) 11-deoxy-7-thia-ω-dihomoprostaglandin $E_1$ methyl ester, tetrahydropyranyl ether, and its 8,12-diepi-isomer.
(86) 11-deoxy-7-thia-16-(m-trifluoromethylphenyl)-17,18,19,20-tetranor-prostaglandin $E_1$ methyl ester, t-butyldimethylsilyl ether, and its 8,12-diepi-isomer.
(87) 11-deoxy-7-thia-17,20-ethanoprostaglandin $E_1$ methyl ester, t-butyldimethylsilyl ether, and its 8,12-diepi-isomer.

EXAMPLE 21

Preparation of 11-deoxy-7-thia-prostaglandin $E_1$ methyl ester of the formulae:

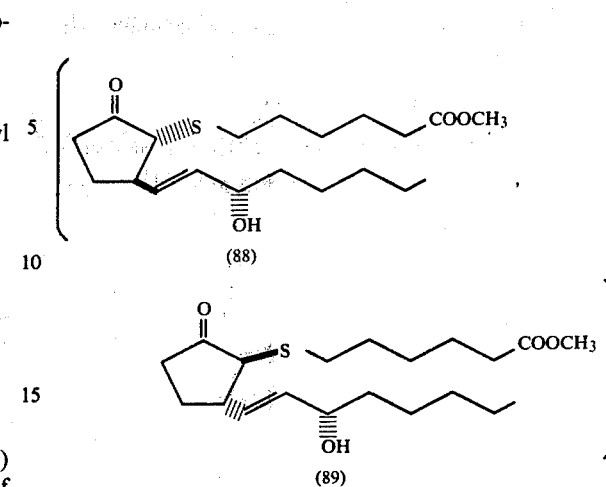

A diastereomeric mixture of 11-deoxy-7-thia-PGE$_1$ methyl ester-15(S)-t-butyldimethylsilyl ether (153 mg) was dissolved in 10 ml of a mixture of acetic acid/water/tetrahydrofuran (3/1/1), and the mixture was stirred at room temperature for 12 hours. A saturated aqueous solution of sodium bicarbonate was added to the reaction mixture to neutralize it, and the mixture was extracted with ethyl acetate. The extract was treated in a customary manner to afford 112 mg of a crude product. The crude product was chromatographed on a thin layer plate with cyclohexane/ethyl acetate (=6/4) to afford 45 mg and 35 mg of compounds corresponding to Rf=0.20 and Rf=0.17.

The total yield of the two compounds was 64%. From the following physical data, these compounds were determined respectively to be 11-deoxy-8,12-diepi-7-thia-PGE$_1$ methyl ester (product 1), and 11-deoxy-7-thia-PGE$_1$ methyl ester (product 2).

Product 1 (compound corresponding to Rf=0.20 in TLC)

IR (film): 3450, 1740, 1260 cm$^{-1}$.
NMR (CCl$_4$, ppm): 0.9(3H, t, J=7 Hz), 1.2–1.8 (16H), 1.9–2.9 (10H), 3.1 (1H, d, J=10 Hz), 3.6 (3H, s), 4.0 (1H, m), 5.55 (2H, m).
Mass (70 eV/m/e): 370 (M$^+$).

Product 2 (compound corresponding to Rf=0.17 in TLC)

IR (film): 3450, 1740, 1260 cm$^{-1}$.
NMR (CCl$_4$, ppm): 0.9 (3H, t, J=7 Hz), 1.2–1.9 (16H), 1.9–2.9 (10H), 3.05 (1H, d, J=10 Hz), 3.6 (3H, s), 4.05 (1H, m), 5.55 (2H, m).
Mass (70 eV, m/e): 370 (M$^+$).

In the same way, the following compounds were prepared.

(90) 11-Deoxy-7-thia-ω-homoprostaglandin $E_1$ methyl ester, and its 8,12-diepi-isomer.
(91) 11-deoxy-7-thia-ω-dihomoprostaglandin $E_1$ methyl ester, and its 8,12-diepi-isomer.
(92) 11-deoxy-7-thia-16-(m-trifluoromethylphenyl)-17,18,19,20-tetranor-prostaglandin $E_1$ methyl ester,
(93) 11-deoxy-7-thia-17,20-ethanoprostaglandin $E_1$ methyl ester, and its 8,12-diepi-isomer.
(94) 11-deoxy-7-thia-16-(m-chlorophenoxy)-17,18,19,20-tetranor-prostaglandin $E_1$ methyl ester, and

(95) 11,15-deoxy-7-thia-19-hydroxyprostaglandin E₁ decyl ester, and its 8,12-diepi-isomer

EXAMPLE 22

Preparation of 15-t-butyldimethylsilyl ether of dl-11-deoxy-15-methyl-7-thia-PGE₁ methyl ester (96) of the formula:

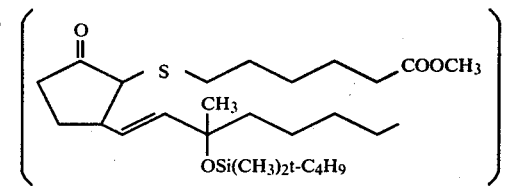

3-t-Butyldimethylsiloxy-1-iodo-3-methyl-oct-1-ene (1140 mg) was dissolved in 10 ml of diethyl ether, and 4.4 ml of t-butyl lithium (as a 1.4 M pentane solution) was added at −78° C. They were reacted for 2 hours. Then, a solution of a copper complex prepared from 482 mg of phenylthio copper, 890 mg of HMP and 5 ml of diethyl ether was added, and reacted at −78° C. for 1 hour. To the resulting lithium organocuprate solution was slowly added dropwise over the course of 10 minutes at −78° C. a diethyl ether solution (5 ml) of 600 mg of 2-(ω-carbomethoxypentylthio)cyclopent-2-en-1-one, and the reaction was performed at −78° C. to −10° C. for 1.5 hours. After the reaction, the reaction mixture was treated in the same way as in Example 20 to afford 2.12 g of a crude product. The crude product was chromatographed on a dry column with hexane/ethyl acetate (=6/4) to afford 210 mg of 15-t-butyldimethylsilyl ether of dl-11-deoxy-15-methyl-7-thia-PGE₁ methyl ester. The product had the following characteristics.

IR (film): 2920, 1745, 1260, 835, 770 cm⁻¹.
NMR (CCl₄, ppm): 0.08 (6H, s), 0.9 (12H, bs), 1.2–2.0 (14H), 1.3 (3H, s), 2.0–3.1 (10H), 3.6 (3H, s), 5.55 (2H, m).
Mass (70 eV, m/e): 498 (M+).

In the same way, the following compounds were prepared.

(97) dl-11-Deoxy-7-thia-3-oxa-4,6-(m- or p-)interphenylene prostaglandin E₁ methyl ester, t-butyldimethylsilyl ether,
(98) dl-11-deoxy-7-thia-3-oxa-4,5-(m- or p-)interphenylene prostaglandin E₁ methyl ester, t-butyldimethylsilyl ether,
(99) dl-11-deoxy-7-thia-2-methyl-3,5-(m- or p-)interphenylene prostaglandin E₁ methyl ester, tetrahydropyranyl ether, and
(100) dl-11-deoxy-7-thia-2,2,15-trimethylprostaglandin E₁ methyl ester, α-ethoxyethyl ether.

EXAMPLE 23

Preparation of dl-11-deoxy-15-methyl-7-thia-PGE₁ methyl ester (101) of the formula:

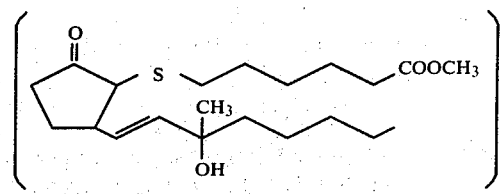

15-t-Butyldimethylsilyl ether of dl-11-deoxy-15-methyl-7-thia-PGE₁ methyl ester (210 mg) was dissolved in 20 ml of a mixture of acetic acid, water and tetrahydrofuran in a ratio of 3:1:1, and the solution was stirred at room temperature for 24 hours. The reaction mixture was neutralized with a saturated aqueous solution of sodium bicarbonate, and extracted with ethyl acetate. The extraxt was treated in a customary manner to afford 170 mg of a crude product. The crude product was chromatographed on a thin layer plate with cyclohexane/ethyl acetate (=6/4) to afford 93 mg of dl-11-deoxy-15-methyl-7-thia-PGE₁ methyl ester in a yield of 58%. The product had the following characteristics.

IR (film): 3450, 1740, 1260 cm⁻¹.
NMR (CCl₄, ppm): 0.9 (3H, t, J=7 Hz), 1.2–1.9 (16H), 1.9–2.9 (10H), 1.28 (3H, s), 3.05 (1H, d, J=10 Hz), 3.6 (3H, s), 5.55 (2H, m).
Mass (70 eV, m/e): 384 (M+).

In the same way, the following compounds were prepared.

(102) dl-11-Deoxy-7-thia-3-oxa-4,6-(,- or p-)interphenylene prostaglandin E₁ methyl ester,
(103) dl-11-deoxy-7-thia-3-oxa-4,5-(m- or p-)interphenylene prostaglandin E₁ methyl ester,
(104) dl-11-deoxy-7-thia-2-methyl-3,5-(m- or p-)interphenylene prostaglandin E₁ methyl ester, and
(105) dl-11-deoxy-7-thia-2,2,15-trimethylprostaglandin E₁ methyl ester.

EXAMPLE 24

Preparation of 7,13-dithia-9-oxoprostanoic acid methyl ester (106) of the formula:

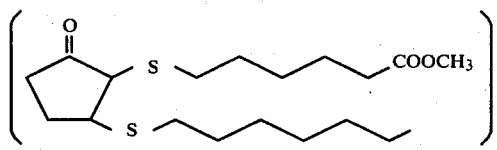

2-(5-Carbomethoxypentylthio)cyclopent-2-en-1-one (336 mg) and 198 mg of n-heptylmercaptan were dissolved in 5 ml of diethyl ether, and 127 mg of piperidine was added. The reaction was performed for 30 minutes. The reaction mixture was poured into 10 ml of an aqueous solution of ammonium chloride, and extracted with diethyl ether. The extract was treated in a customary manner to afford 540 mg of a crude product. The crude product was chromatographed on a thin layer plate with cyclohexane/ethyl acetate (=8/2) to afford 264 mg of methyl 7,13-dithia-9-oxoprostanoate in a yield of 51%. The product had the following characteristics
IR (film): 1740, 1170 cm⁻¹.
NMR (CCl₄, ppm): 0.9 (3H, t), 1.2–1.9 (16H), 2.1–3.3 (12H), 3.6 (3H, s).

In the same way, the following compounds were prepared.

(107) Methyl 7,13-dithia-9-oxo-ω-homoprostanoate,
(108) methyl 7,13-dithia-9-oxo-2,3,4-trinor-prostanoate,
(109) methyl 7,13-dithia-9-oxo-16-phenyl-2,3,4,17,18,19,20-heptanor-prostanoate,
(110) 2,3-bis(β-methoxycarbonylethylthio)cyclopentanone,
(111) methyl 7,13-dithia-9-oxo-3-oxa-4,5-(m- or p-) interphenylene prostanoate,
(112) methyl 7,13-dithia-9-oxo-3-oxa-2-methyl-4,6-(m- or p-)interphenylene prostanoate, and
(113) methyl 7,13-dithia-9-oxo-3,5-(m- or p-)interphenylene prostanoate.

EXAMPLE 25

Preparation of 7,13-dithia-9-oxoprostanoic acid (114) of the formula:

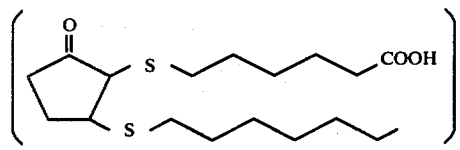

2-(5-Carboxypentylthio)cyclopent-2-en-1-one (180 mg) and 106 mg of n-heptylmercaptan were dissolved in 10 ml of diethyl ether, and 255 mg of morpholine was added. The reaction was performed at room temperature for 12 hours. An aqueous solution of ammonium chloride was added to the reaction mixture, and the aqueous solution was acidified with 5% hydrochloric acid. By the same treatment as in Example 24, 230 mg of a crude product was obtained. The crude product was chromatographed on a thin layer plate with cyclohexane/ethyl acetate (=6/4) to afford 65 mg of 7,13-dithia-9-oxoprostanoic acid in a yield of 23%. The product had the following characteristics.

IR (film): 1740, 1715 cm$^{-1}$.
NMR (CCl$_4$, ppm): 0.9 (3H, t), 1.2–1.9 (16H), 2.1–3.3 (12H), 10.4 (1H, bs).

In the same way, the following compounds were prepared.

(115) 7,13-Dithia-9-oxo-ω-homoprostanoic acid,
(116) 7,13-dithia-9-oxo-2,3,4-trinor-prostanoi acid,
(117) 7,13-dithia-9-oxo-16-phenyl-2,3,4,17,18,19,20-heptanor-prostanoic acid,
(118) 2,3-bis(β-carboxyethylthio)cyclopentanone,
(119) 7,13-dithia-9-oxo-3-oxa-4,5-(m- or p-)interphenylene prostanoic acid,
(120) 7,13-dithia-9-oxo-3-oxa-2-methyl-4,6-(m- or p-) interphenylene prostanoic acid, and
(121) 7,13-dithia-9-oxo-3,5-(m- or p-)interphenylene prostanoic acid.

EXAMPLE 26

Preparation of 7,13-dithia-11-oxo-prostanoic acid (122) of the formula:

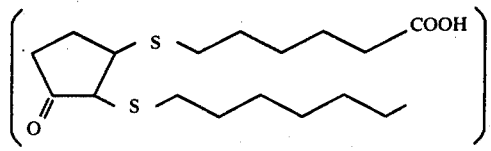

2-n-Heptylthiocyclopent-2-en-1-one (222 mg) and 155 mg of ω-mercaptocaproic acid were dissolved in 5 ml of diethyl ether, and 173 mg of piperidine was added. The reaction was performed at room temperature for 12 hours. The reaction mixture was treated in the same way as in Example 25 to afford 36. mg of a crude product. The crude product was chromatographed on a thin layer plate with benzene/methanol (=9/1) to afford 127 mg of 7,13-dithia-11-oxo-prostanoic acid in a yield of 34%. The product had the following characteristics.

IR (film): 1740, 1715 cm$^{-1}$.
NMR (CCl$_4$, ppm): 0.9 (3H, t), 1.2–1.9 (6H), 2.1–3.3 (12H), 10.8 (1H, bs).

In the same way, the following compounds were prepared.

(123) 7,13-Dithia-11-oxo-2,3,4,5-tetranor-prostanoic acid,
(124) 7,13-dithia-11-oxo-2,3,4-trinor-prostanoic acid,
(125) 7,13-dithia-11-oxo-3,-oxa-4,5-(m- or p-)interphenylene prostanoic acid,
(126) 7,13-dithia-11-oxo-2-methyl-3-oxa-4,6-(m- or p-) interphenylene prostanoic acid, and
(127) 7,13-dithia-11-oxo-3,5-(m- or p-)interphenylene prostanoic acid.

EXAMPLE 27

Preparation of methyl 7,13-dithia-11-oxo-prostanoate (128) of the formula:

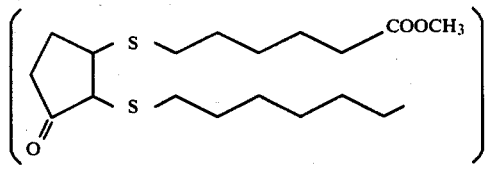

2-n-Heptylthiocyclopent-2-en-1-one (212 mg) and 162 mg of methyl ω-mercaptocaproate were dissolved in 5 ml of methanol, and 87 mg of morpholine was added. They were reacted at room temperature for 12 hours. The reaction mixture was treated in the same way as in Example 24 to afford 383 mg of a crude product. The crude product was chromatographed on a thin layer plate with cyclohexane/ethyl acetate (=8/2) to afford 177 mg of methyl 7,13-dithia-11-oxo-prostanoate in a yield of 47%. The product has the following characteristics.

IR (film): 1740 cm$^{-1}$.
NMR (CCl$_4$, ppm): 0.9 (3H, t), 1.2–1.9 (16H), 2.1–3.3 (12H), 3.6 (3H, s).

In the same way, the following compounds were prepared.

(129) Methyl 7,13-dithia-11-oxo-2,3,4,5-tetranorprostanoate,
(130) decyl 7,13-dithia-11-oxo-2,3,4-trinorprostanoate, (131) methyl 7,13-dithia-11-oxo-3-oxa-4,5-(m- or p-)interphenylene prostanoate,
(132) methyl 7,13-dithia-11-oxo-2-methyl-3-oxa-4,6-(m- or p-)interphenyleneprostanoate, and
(133) methyl 7,13-dithia-11-oxo-3,5-(m- or p-)interphenylene prostanoate.

EXAMPLE 28

Preparation of methyl 7,13-dithia-9-oxo-16-phenyl-17,18,19,20-tetranor-prostanoate (134) of the formula

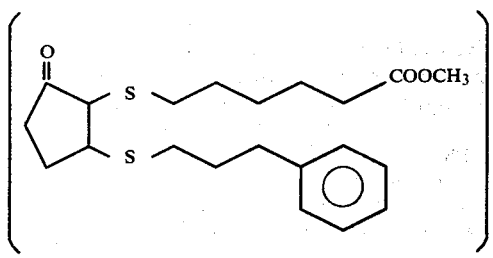

2-(5-Carbomethoxypentylthio)cyclopent-2-en-1-one (178 mg) and 135 mg of γ-phenylpropylmercaptan were dissolved in 5 ml of methanol, and two drops of piperidine were added. They were reacted at room temperature for 1 hour. After the reaction, the reaction mixture was treated in the same way as in Example 24 to afford 327 mg of a crude product. The crude product was chromatographed on a thin layer plate with hexane/ethyl acetate (=8/2) to afford 95 mg of methyl 7,13-dithia-9-oxo-16-phenyl-17,18,19,20-tetranor-prostanoate in a yield of 31%. The product had the following characteristics.

IR (film): 1735 cm$^{-1}$.
NMR (CCl$_4$, ppm): 1.3–2.0 (8H), 2.1–3.3 (14H), 3.6 (3H, s).

In the same way, the following compounds were prepared.

(135) Methyl 7,13-dithia-9-oxo-15-(m-trifluoromethylphenoxy)-16,17,18,19,20-pentanor-prostanoate, and
(136) methyl 7,13-dithia-9-oxo-15-(p-hydroxyphenyl)-16,17,18,19,20-pentanor-prostanoate.

EXAMPLE 29

Preparation of 7,13-dithia-9-hydroxy-11-oxo-prostanoic acid (137) of the formula

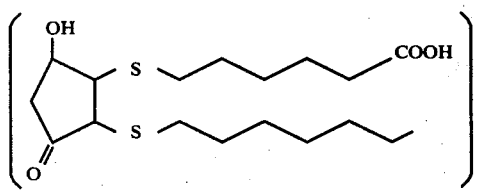

2-(n-Heptylthio)-4-hydroxycyclopent-2-en-1-one (23 mg) and 15 mg of ω-mercaptocaproic acid were dissolved in 2 ml of diethyl ether, and 19 ml of piperidine was added. They were reacted at room temperature for 1 hour. An aqueous solution of ammonium chloride was added, and the mixture was extracted with diethyl ether. The ethereal layer was treated in a customer customary manner to afford 50 mg of a crude product. The crude product was chromatographed on a thin layer plate with ethyl acetate/benzene (=4/6) to afford 4 mg of 7,13-dithia-9-hydroxy-11-oxo-prostanoic acid in a yield of 13%.

IR (film): 1735, 1710 cm$^{-1}$.
(NMR (CCl$_4$, ppm): 0.9 (3H, t), 1.2–1.9 (16H), 2.1–3.3 (10H), 4.1 (1H, m), 10.1 (2H, bs).

In the same way, the following compounds were prepared.

(138) 7,13-Dithia-9-hydroxy-11-oxo-2,3,4,5-tetranor-prostanoic acid,
(139) 7,13-dithia-9-hydroxy-11-oxo-2,3,4-trinorprostanoic acid,
(140) 7,13-dithia-9-hydroxy-11-oxo-3-oxa-4,5-(m- or p-)interphenylene prostanoic acid,
(141) 7,13-dithia-9-hydroxy-11-oxo-2-methyl-3-oxa-4,6-(m- or p-)interphenylene prostanoic acid, and
(142) 7,13-dithia-9-hydroxy-11-oxo-3,5-(m- or p-)interphenylene prostanoic acid.

EXAMPLE 30

Preparation of methyl 7,13-dithia-15-hydroxy-15-methyl-9-oxo-prostanoate (143) of the formula:

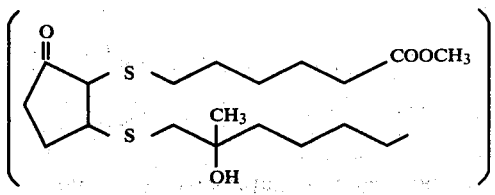

2-(5-Carbomethoxypentylthio)cyclopentenone (172 mg) and 162 mg of 2-hydroxy-2-methylheptylmercaptan (162 mg) were dissolved in 2 ml of diethyl ether, and 60 mg of piperidine was added. They were reacted for 1 hour. After the reaction, the reaction mixture was treated in the same way as in Example 24 to afford 308 mg of a crude product. The crude product was chromatographed on a thin layer plate with hexane/ethyl acetate (=6/4) to afford 102 mg of a product in a yield of 25%. It was found that this product contained about 60% of methyl 7,13-dithia-15-hydroxy-15-methyl-9-oxo-prostanoate at Rf=0.70 in TLC.

In the same way, the following compounds were prepared.

(144) Methyl 7,13-dithia-15-hydroxy-15-methyl-9-oxo-ω-trihomoprostanoate,
(145) methyl 7,13-dithia-15-hydroxy-15-methyl-9-oxo-15(p-fluorophenoxy)-16,17,18,19,20-pentanor-prostanoate, and
(146) methyl 7,13-dithia-15-hydroxy-15-methyl-9-oxo-16-(p-fluorophenyl)-17,18,19,20-tetranor-prostanoate.

EXAMPLE 31

Preparation of methyl 7,13-dithia-11,15-dihydroxy-15-methyl-9-oxo-prostanoate (147) of the formula:

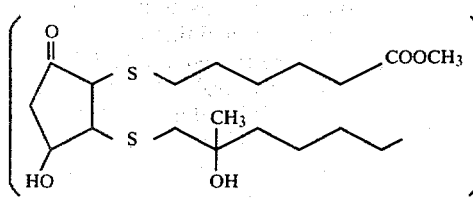

2-(5-Carbomethoxypentylthio)-4-hydroxycyclopent-2-en-1-one (60 mg) and 37 mg of 2-hydroxy-2-methylheptylmercaptan were dissolved in 2 ml of methanol, and one drop of piperidine was added. The mixture was allowed to stand at room temperature for 20 minutes. The reaction mixture was treated in the same way as in Example 24 to afford 99 mg of a crude product. The crude product was chromatographed on a thin layer plate with cyclohexane/ethyl acetate (=4/6) to afford 36 mg of a product in a yield of 27%. It was found that this product contained about 55% of methyl 7,13-dithia-11,15-dihydroxy-15-methyl-9-oxo-prostanoate at Rf=0.35.

In the same way, the following compounds were prepared.

(148) Methyl 7,13-dithia-11,15-dihydroxy-15-methyl-9-oxo-ω-homoprostanoate, (149) methyl 7,13-dithia-11,15-dihydroxy-15-methyl-9-oxo-15-(p-fluorophenoxy)-16,17,18,19,20-pentanor-prostanoate, and (150) methyl 7,13-dithia-11,15-dihydroxy-15-methyl-9-oxo-16-(p-fluorophenyl)-17,18,19,20-tetranor-prostanoate.

EXAMPLE 32

Preparation of methyl 7,13-dithia-11-hydroxy-9-oxo-prostanoate (151) of the formula:

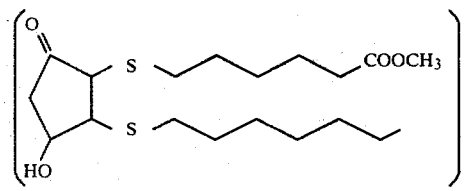

2-(5-Carbomethoxypentylthio)-4-hydroxycyclopent-2-en-1-one (26 mg) and 14 mg of n-heptylmercaptan were dissolved in 2 ml of diethyl ether, and one drop of piperidine was added. They were reacted for 1 hour. The reaction mixture was treated and purified in the same way as in Example 24 to afford 12 mg of a product in a yield of 30%. By thin-layer chromatography (ethyl acetate/cyclohexane=6/4), this product was found to contain methyl 7,13-dithia-11-hydroxy-9-oxo-prostanoate of 90% purity at Rf=0.45. The product had the following characteristics.

IR (film): 3350, 1745 cm$^{-1}$.

NMR (CCl$_4$, ppm): 0.9 (3H, t), 1.2–1.8 (16H), 2.1–3.2 (1H), 3.6 (3H, s), 4.1 (1H, m).

In the same way, the following compounds were prepared.

(152) Methyl 7,13-dithia-11-hydroxy-9-oxo-ω-homoprostanoate, and (153) decyl 7,13-dithia-11-hydroxy-9-oxo-16-phenyl-17,18,19,20-tetranor-prostanoate.

EXAMPLE 33

Preparation of 7,13-dithia-15-hydroxy-15-methyl-11-oxo-prostanoic acid (154) of the formula:

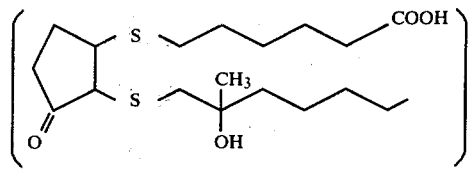

2-(2-Hydroxy-2-methylheptylthio)cyclopent-2-en-1-one (130 mg) and 110 mg of ω-mercaptocaproic acid were dissolved in 3 ml of a methanol, and 100 ml of pyridine was added. The mixture was allowed to stand at room temperature for 2 hours. After the reaction, the solvent was distilled off to afford 300 mg of a crude product. The crude product was chromatographed on a thin layer plate with cyclohexane/ethyl acetate (=4/6) to afford 138 mg of a compound having a spot corresponding to Rf=0.35 in a yield of 65%. This compound was determined to be 7,13-dithia-15-hydroxy-15-methyl-11-oxo-prostanoic acid from the following data.

IR (film): 3400, 1735, 1710 cm$^{-1}$.

NMR (CCl$_4$, ppm): 0.9 (3H, t, J=7 Hz), 1.2 (3H, s), 1.1–2.0 (14H), 2.0–3.2 (10H), 2.9 (2H, s), 6.8 (2H, bs).

In the same way, the following compounds were prepared.

(155) 7,13-Dithia-15-hydroxy-15-methyl-11-oxo-2,3,4-trinor-prostanoic acid, (156) 7,13-dithia-15-hydroxy-15-methyl-11-oxo-3-oxa-4,5-(m- or p-)interphenylene prostanoic acid, (157) 7,13-dithia-15-hydroxy-15-methyl-11-oxo-2-methyl-3-oxa-4,6-(m- or p-)interphenylene prostanoic acid, and (158) 7,13-dithia-15-hydroxy-15-methyl-11-oxo-3,5-(m- or p-)interphenylene prostanoic acid.

EXAMPLE 34

Production of methyl 7,13-dithia-11-hydroxyprostanoate (159) of the formula:

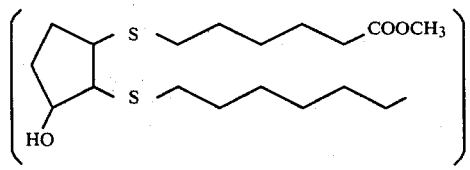

2-n-Heptythiocyclopent-2-en-1-one (212 mg) and 180 mg of methyl ω-mercaptocaproate were dissolved in 3 ml of tetrahydrofuran, and two drops of piperidine were added. The mixture was reacted at room temperature for 1 hour. The reaction mixture was cooled to −78° C., and 1.5 ml of lithium triisobutyl borohydride (as a 1 M tetrahydrofuran solution) was added, after which the reaction was performed at −70° C. for 1 hour. After the reaction, 0.5 ml of a 3 N aqueous solution of sodium hydroxide was added, and then 0.6 ml of 30% hydrogen peroxide was further added. The mixture was reacted at 0° C. for 30 minutes, and then at room temperature for 12 hours. The reaction mixture was poured into a saturated aqueous solution of ammonium chloride, and extracted twice with diethyl ether, and then twice with ethyl acetate. The extracts were treated in a customary manner to afford 420 mg of a crude product. The crude product was chromatographed on a thin layer plate with cyclohexane/diethyl ether (=6/4) to afford 45 mg of a product coresponding to Rf=0.33 in a yield of 12%. From the following characteristics, this product was determined to be methyl 7,13-dithia-11-hydroxyprostanoate.

IR (film): 3450, 1740, 1200, 790 cm$^{-1}$.

NMR (CCl$_4$, ppm): 0.9 (3H, t, J=7 Hz), 1.1–20 (16H), 2.0–3.0 (13H), 3.60 (3H, s), 4.0 (1H, m).

Mass (70 eV, m/e): 387 (M+).

In the same way, the following compounds were produced.

(160) Methyl 7,13-dithia-11-hydroxy-2,3,4,5-tetranor-prostanoate, and
(161) decyl 7,13-dithia-11-hydroxy-2,3,4-trinorprostanoate.

EXAMPLE 35

Preparation of methyl 7,13-dithia-11-hydroxyprostanoate (159):

2-n-Heptylthiocyclopent-2-en-1-one (510 mg) and 390 mg of methyl ω-mercaptocaproate were dissolved in 3 ml of methanol, and 40 ml of piperidine was added. The mixture was reacted at room temperature for 1 hour, and the reaction mixture was further reacted with 100 mg of sodium borohydride at 0° C. for 1 hour. After the reaction, the reaction mixture was poured into a saturated aqueous solution of ammonium chloride, and extracted with ethyl acetate. The extract was treated in a customary manner to afford 900 mg of a crude product. The crude product was chromatographed on a thin layer plate with cyclohexane/ethyl acetate (=6/4) to afford 200 mg, 243 mg and 208 mg of products having spots corresponding to Rf=0.33, Rf=0.30, and Rf=0.27 respectively in a total yield of 70%.

From the IR, NMR and mass data, they were found to be stereoisomers. The data of the product corresponding to Rf=0.33 were identical to those of the product obtained by the procedure of Example 34.

In the same way, the following compounds were prepared.

(162) Methyl 7,13-dithia-11-hydroxy-3-oxa-4,5-(m- or p-)interphenylene prostanoate,
(163) methyl 7,13-dithia-11-hydroxy-2-methyl-3-oxa-4,6-(m- or p-)interphenylene prostanoate, and
(164) methyl 7,13-dithia-11-hydroxy-3,5-(m- or p-) interphenylene prostanoate.

EXAMPLE 36

Preparation of 7,13-dithia-11-hydroxyprostanoic acid (165) of the formula:

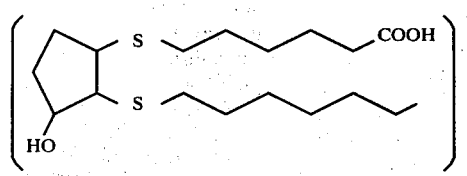

Methyl 7,13-dithia-11-hydroxyprostanoate (30 mg) was dissolved in 2.5 ml of methanol, and 1.0 ml of a 0.1 N aqueous solution of sodium hydroxide was added. The mixture was reacted at room temperature for 15 hours. The reaction mixture was acidified with dilute hydrochloric acid, and extracted three times with ethyl acetate. The extracts were treated in a customary manner to afford 26 mg of 7,13-dithia-11-hydroxyprostanoic acid in a yield of 90%. The product had the following characteristics.

IR (film): 3400, 1715 cm$^{-1}$.

NMR (CCl$_4$, ppm): 0.9 (3H, t, J=7 Hz), 1.0–2.0 (16H), 2.0–3.0 (12H), 4.0 (1H, m), 6.9 (2H, bs).

In the same way, the following compounds were prepared.

(166) 7,13-Dithia-11-hydroxy-2,3,4,5-tetranor-prostanoic acid,
(167) 7,13-dithia-11-hydroxy-2,3,4-trinor-prostanoic acid,
(168) 7,13-dithia-11-hydroxy-3-oxa-4,5-(m- or p-)interphenylene prostanoic acid,
(169) 7,13-dithia-11-hydroxy-2-methyl-3-oxa-4,6-(m- or p-)interphenylene prostanoic acid, and
(170) 7,13-dithia-11-hydroxy-3,5-(m- or p-)interphenylene prostanoic acid.

EXAMPLE 37

Preparation of methyl 7,13-dithia-9-hydroxyprostanoate (171) of the formula:

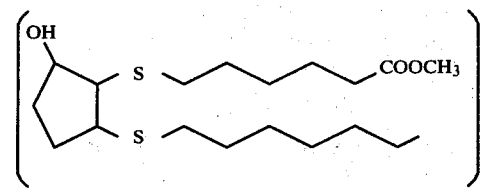

2-(5-Carbomethoxypentylthio)cyclopent-2-en-1-one (116 mg) and 64 mg of n-heptylmercaptan were dissolved in 2 ml of methanol, and 14 mg of piperidine (two drops) was added. The mixture was reacted at room temperature for 40 minutes. The reaction mixture was further reacted with 20 mg of sodium borohydride at room temperature for 20 minutes. After the reaction, the reaction mixture was treated by the same procedure as in Example 35 to afford 146 mg of a crude product. The crude product was chromatographed on a thin layer plate with cyclohexane/ethyl acetate (=8/2) to afford 24 mg, 60 mg and 10 mg of products corresponding to Rf=0.35, Rf=0.32, and Rf=0.28 respectively in a total yield of 52%. From the IR, NMR, and mass data, these products were found to be stereoisomers of methyl 7,13-dithia-9-hydroxyprostanoate. The product corresponding to Rf=0.35 had the following characteristics.

IR (film): 3450, 1740, 1210 cm$^{-1}$.

NMR (CCl$_4$, ppm): 0.9 (3H, t, J=7 Hz), 1.1–2.0 (20H), 2.0–2.9 (9H), 3.60 (3H, s), 4.0 (1H, m).

Mass (70 eV, m/e): 976 (M+).

It was also found from NMR and mass spectra that the product corresponding to Rf=0.32 contained 2-(5-carbomethoxypentylthio)cyclopentan-1-ol.

In the same way, the following compounds were prepared.

(172) Methyl 7,13-dithia-9-hydroxy-ω-homoprostanoate,
(173) methyl 7,13-dithia-9-hydroxy-2,3,4-trinor-prostanoate,
(174) methyl 7,13-dithia-9-hydroxy-16-phenyl-2,3,4,17,18,19,20-heptanor-prostanoate,
(175) methyl 7,13-dithia-9-hydroxy-3-oxa-4,5-(m- or p-)interphenylene prostanoate,
(176) 2,3-bis(β-methoxycarbonylethylthio)cyclopentanol,
(177) methyl 7,13-dithia-9-hydroxy-3-oxa-2-methyl-4,6-(m- or p-)interphenylene prostanoate, and
(178) methyl 7,13-dithia-9-hydroxy-3,5-(m- or p-)interphenylene prostanoate.

EXAMPLE 38

Methyl 7,13-dithia-9,11-dihydroxyprostanoate (179) of the formula:

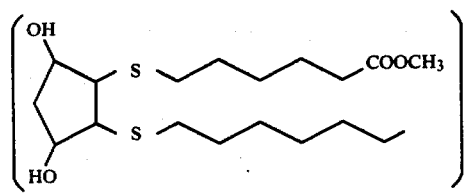

2-(5-Carbomethoxypentylthio)-4-hydroxycyclopent-2-en-1-one (90 mg) and 56 mg of n-heptylmercaptan were dissolved in 2 ml of tetrahydrofuran, and one drop (8 mg) of piperidine was added. The mixture was reacted at room temperature for 1 hour. The mixture was added dropwise at 0° C. to 2 ml of a methanol solution of 30 mg of sodium borohydride, and reacted at room temperature for 1 hour. After the reaction, the reaction mixture was treated in the same way as in Example 35 to afford 90 mg of a crude product. The product was chromatographed on a thin layer plate with cyclohexane/ethyl acetate (=6/4) to afford 15 mg of a product corresponding to Rf=0.45 in a yield of 11%. From the following characteristics, this product was determined to be methyl 7,13-dithia-9,11-dihydroxyprostanoate.

IR (film): 3450, 1740, 1200, 1090 cm$^{-1}$.
NMR (CCl$_4$, ppm): 0.9 (3H, t, J=7 Hz), 1.1–2.1 (16H), 2.1–3.2 (12H), 3.6 (3H, s), 4.05 (2H, m).
Mass (70 eV, m/e): 392 (M$^+$)

In the same way, the following compounds were prepared.

(180) Methyl 7,13-dithia-9,11-dihydroxy-9-oxo-ω-homoprostanoate, and
(181) decyl 7,13-dithia-9,11-dihydroxy-9-oxo-16-phenyl-17,18,19,20-tetraor-prostanoate.

EXAMPLE 39

Preparation of methyl 7,13-dithia-9,15-dihydroxy-15-methylprostanoate (182) of the formula:

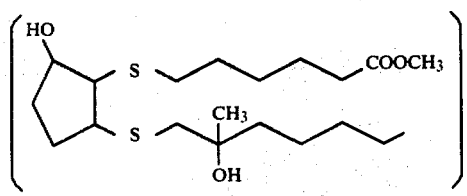

2-(5-Carbomethoxypentylthio)cyclopent-2-en-1-one (145 mg) and 100 mg of 2-hydroxy-2-methylheptylmercaptan were dissolved in 2 ml of methanol, and the mixture was stirred at room temperature for 20 minutes. The reaction mixture was added dropwise at 0° C. to 1 ml of a methanol solution of 60 mg of sodium borohydride. The mixture was stirred at 0° C. for 30 minutes, and then at room temperature for an additional 30 minutes. After the reaction, the reaction mixture was treated in the same way as in Example 35 to afford 260 mg of a crude product. The crude product was chromatographed on a thin layer plate with cyclohexane/ethyl acetate (=6/4) to afford 28 mg, 58 mg and 28 mg of products corresponding to spots Rf=0.30, Rf=0.27, and Rf=0.24 respectively in a total yield of 47%. From the IR, NMR and mass data, these three products were found to be stereoisomers of methyl 7,13-dithia-9,15-dihydroxy-15-methylprostanoate. The product corresponding to RF=0.27 had the following properties.

IR (film): 3450, 1740, 1200 cm$^{-1}$.
NMR (CCl$_4$, ppm): 0.9 (3H, t, J=7 Hz), 1.15 (3H, s), 1.0–2.0 (18H), 2.0–3.1 (10H), 3.6 (3H, s), 4.05 (1H, m).
Mass (70 eV, m/e): 406 (M$^+$).

From the NMR and mass spectra, the product corresponding to Rf=0.30 contained 2-(5-carbomethoxypentylthio)cyclopent-2-en-1-ol.

In the same way, the following compounds were prepared.

(183) Methyl 7,13-dithia-9,15-dihydroxy-15-methyl-ω-trihomoprostanoate,
(184) methyl 7,13-dithia-9,15-dihydroxy-15-methyl-15-(p-fluorophenoxy)-16,17,18,19,20-pentanor-prostanoate, and (185) methyl 7,13-dithia-9,15-dihydroxy-15-methyl-16-(p-fluorophenyl)-17,18,19,20-tetranor-prostanoate.

EXAMPLE 40

Preparation of methyl 7,13-dithia-15-methyl-9,11,15-trihydroxyprostanoate (186) of the formula:

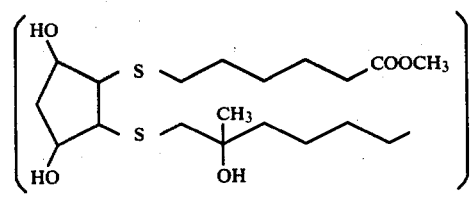

2-(5-Carbomethoxypentylthio)-4-hydroxycyclopent-2-en-1-one (258 mg) and 180 mg of 2-hydroxy-2-methylheptylmercaptan were dissolved in 3 ml of tetrahydrofuran and 21 ml of methanol, and reacted at room temperature for 30 minutes. The reaction mixture was further reacted with 70 mg of sodium borohydride at 0° C. for 30 minutes, and then at room temperature for 1 hour. The reaction mixture was treated in the same way as in Example 35 to afford 360 mg of a crude product. The crude product was chromatographed on a thin layer plate with cyclohexane/ethyl acetate (=2/8) to afford 53 mg of methyl 7,13-dithia-15-methyl-9,11,15-trihydroxyprostanoate in a yield of 13%. The product had the following characteristics.

IR (film): 3350, 1740 cm$^{-1}$.

NMR (CCl₄, ppm): 0.90 (3H, t, J=6 Hz), 1.20 (3H, s), 1.2-2.0 (14H), 2.0-3.0 (10H), 3.1-3.8 (3H), 3.60 (3H, s), 4.05 (2H, bs).

Mass (12 eV, m/e): 404 (M⁺ −18).

In the same way, the following compounds were prepared.

(187) Methyl 7,13-dithia-9,11,15-trihydroxy-15-methyl-ω-homoprostanoate,
(188) methyl 7,13-dithia-9,11,15-trihydroxy-15-methyl-15-(p-fluorophenoxy)-16,17,18,19,20-pentanor-prostanoate, and
(189) methyl 7,13-dithia-9,11,15-trihydroxy-15-methyl-16-(p-fluorophenyl)-17,18,19,20-tetranor-prostanoate.

EXAMPLE 41

Preparation of methyl 7,13-dithia-11-hydroxy-16-phenyl-17,18,19,20-tetranor-prostanoate (190) of the formula:

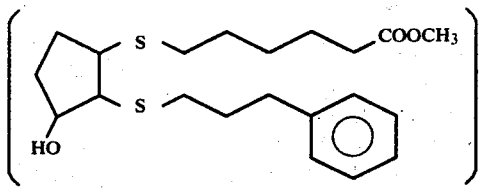

2-(3-Phenylpropylthio)cyclopent-2-en-1-one (132 mg) and 110 mg of methyl ω-mercaptocaproate were dissolved in 2 ml of methanol, and reacted at room temperature for 1 hour. Then, 65 mg of sodium borohydride was added at 0° C. The mixture was further reacted at room temperature for 1 hour, and treated in the same way as in Example 35 to afford 225 mg of a crude product. The crude product was chromatographed on a thin layer plate with cyclohexane/ethyl acetate (=6/4) to afford 88 mg of methyl 7,13-dithia-11-hydroxy-16-phenyl-17,18,19,20-tetranor-prostanoate in a yield of 39%. The product had the following characteristics.

IR (film): 3450, 3030, 1740, 750, 690 cm⁻¹.

NMR (CCl₄, ppm): 1.2-3.3 (23H), 3.60 (3H, s), 3.95 (1H, bs), 7.15 (5H, s).

Mass (70 eV, m/e): 396 (M⁺).

In the same way, the following compounds were prepared.

(191) Methyl 7,13-dithia-9-hydroxy-15-(m-trifluoromethylphenoxy)-16,17,18,19,20-pentanor-prostanoate, and
(192) methyl 7,13-dithia-9-hydroxy-15-(p-hydroxyphenyl)-16,17,18,19,20-pentanor-prostanoate.

REFERENTIAL EXAMPLE 1

(Action of inhibiting the formation of ulcer)

By the method of Y. H. Lee et al. [Arch. Int. Pharmacodyn. Ther., 192, 370 (1971)], the inhibiting action of dl-11-deoxy-15-methyl-7-thia-PGE₁ methyl ester (a compound of formula II) on the formation of ulcer in rats induced by indomethacin, a typical non-steroid anti-inflammatory agent, was evaluated. As shown in Table 1 below, this compound markedly inhibited ulcer formation.

Male rats (Sprague Dawley species; body weight 300 g) were used in the experiment. These rats had been caused to fast for 24 hours in separate cages before the initiation of the experiment. Indomethacin was orally administered to these rats, and 6 hours later, they were killed. Formation of ulcer in the fundus part was examined by measuring the area of the ulcer-forming part under microscope. The dl-11-deoxy-15-methyl-7-thia-PGE₁ methyl ester was orally administered at the end of 30 minutes and 3 hours, respectively, after the administration of indomethacin. The ulcer formation inhibiting rate of the dl-11-deoxy-15-methyl-7-thia-PGE₁ methyl ester against a predetermined dose of indomethacin was determined.

The indomethacin was administered as a 0.5 ml aqueous suspension (containing two drops of a Tween-type nonionic surfactant per 14 ml of water). The dl-11-deoxy-15-methyl-7-thia-PGE₁ methyl ester was given in the form of a solution in a phosphate buffer containing 0.9% of sodium chloride.

Table 1 shows the inhibition, by dl-11-deoxy-15-methyl-7-thia-PGE₁ methyl ester, of ulcer formation induced by indomethacin (20 mg/kg, peroral). The results show that this compound has an ED₅₀ of 0.3 mg/kg.

Table 1

| Compound | Dose (mg/kg,po) | Number of rats | Ulcer formation (ulcer coefficient) Average value ± S.E.M. | Inhibiting rate (%) |
|---|---|---|---|---|
| None (control) | Zero | 7 | 68.7 ± 10.3 | 0 |
| dl-11-deoxy-15-methyl-7-thia PGE₁ methyl ester (compound No. 101) | 0.1 | 7 | 57.5 ± 14.1 | 16 |
| dl-11-deoxy-15-methyl-7-thia PGE₁ methyl ester (compound No. 101) | 0.4 | 7 | 23.3 ± 12.4*** | 66 |
| dl-11-deoxy-15-methyl-7-thia PGE₁ methyl ester (compound No. 101) | 1.0 | 7 | 0.6 ± 0.05*** | 99 |

***shows p 0.001; S.E.M. shows a standard error of the mean value.

REFERENTIAL EXAMPLES 2 TO 8

In the same way as in Referential Example 1, the compounds shown in Table 2 were examined for their inhibiting action on ulcer formation. The results are shown in Table 2. With some of these compounds, acute toxicity (iv) in mice is also shown in Table 2. The acute toxicity LD₅₀ of PGF₂α is 60 mg/kg (male), and 56 mg/kg (female).

Table 2

| Referential Example | Compound | Dose (mg/kg, po) | Inhibiting rate (%) | LD₅₀ |
|---|---|---|---|---|
| 2 | Methyl 7,13-dithia-9-hydroxy-prostanoate (No. 171) | 0.4 5.0 | 12 75 | — |
| 3 | 7,13-Dithia-15-hydroxy-15-methyl-11-oxoprostanoic acid (No. 154) | 0.4 2.0 | 10 80 | 350 |
| 4 | Methyl 7,13-dithia-11- | 0.4 | 15 | |

Table 2-continued

| Referential Example | Compound | Dose (mg/kg, po) | Inhibiting rate (%) | LD$_{50}$ |
|---|---|---|---|---|
| | hydroxyprostanoate (No. 159) | 2.0 | 78 | — |
| 5 | Methyl 7,13-dithia-9,15-dihydroxy-15-methylprostanoate (No. 182) | 0.4<br>2.0 | 25<br>80 | — |
| 6 | 11-Deoxy-7-thia-8,12-diepiprostaglandin E$_1$ methyl ester (No. 89) | 0.4<br>1.0 | 57<br>65 | 20 |
| 7 | 11-Deoxy-7-thiaprostaglandin E$_1$ methyl ester (No. 88) | 0.4 | 73 | — |
| 8 | Methyl 7,13-dithia-11-hydroxy-16-phenyl-17,18,19,20-tetranorprostanoate (No. 190) | 0.4<br>1.0 | 46<br>57 | — |

What we claim is:

1. Organodithiocyclopentanes having the formula

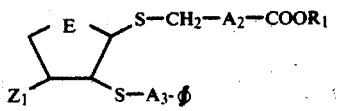

wherein A$_1$, E, A$_2$ and R$_1$ are as defined above, A$_3$ represents a saturated divalent aliphatic hydrocarbon group containing 1 to 5 carbon atoms which may contain, as a substituent, a hydroxyl group or a protected hydroxyl group; and $\phi$ represents a phenyl group, cyclohexyl group or cyclopentyl group, which groups may optionally contain one or two trifluoromethyl groups, an hydroxyl group or a halogen atom, or a group of the formula

wherein R$_1$ is as defined above, A$_1$ represents a divalent saturated or unsaturated aliphatic hydrocarbon group containing 1 to 3 carbon atoms; and, n is 0 or 1, and when n is 0, $+$COOR$_1$)n represents a hydrogen atom.

2. Organodithiocyclopentanes of the formula

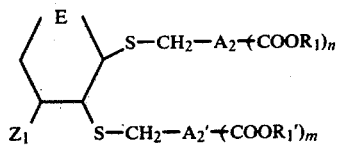

wherein E represents $>$C$=$O or

in which Z' represents a hydrogen atom, a hydroxyl group or a protected hydroxyl group; A$_2$ represents a saturated or unsaturated divalent aliphatic hydrocarbon group containing 1 to 13 carbon atoms; A$_2$' represents a saturated or unsaturated hydrocarbon group containing 1 to 13 carbon atoms which may contain, as a substituent, a hydroxyl group or a protected hydroxyl group; R$_1$ and R$_1$' may be identical to or different from each other, and represent a hydrogen atom or a saturated or unsaturated aliphatic hydrocarbon group containing 1 to 10 carbon atoms; m represents 0 or 1, n represents 0 or 1 with the proviso that at least one of m or n is 1 and when m is 0, $+$COOR$_1$')$_m$ represents a hydrogen atom; said protected hydroxyl groups being identical to or different from each other and selected from the group consisting of 5-butyldimethylsiloxy, trimethylsiloxy, tribenzylsiloxy, 2-tetrahydrooxypyranyloxy, 2-tetrahydrofuranyloxy and 1-ethoxyethyloxy.

3. 7,13-dithia-15-hydroxy-15-methyl-11-oxo-prostanoic acid.

* * * * *

UNITED STATES PATENT AND TRADEMARK OFFICE
CERTIFICATE OF CORRECTION

PATENT NO. : 4,180,672
DATED : December 25, 1979
INVENTOR(S) : KUROZUMI, ET AL.

It is certified that error appears in the above-identified patent and that said Letters Patent are hereby corrected as shown below:

In line 8 of the Abstract, delete ">C=O" and insert -- $\diagup\!\!\!\!\diagdown\!\!\!\!\!\text{C}=\text{O}$ --

In claim 2, line 15, delete ">C=O" and insert -- $\diagup\!\!\!\!\diagdown\!\!\!\!\!\text{C}=\text{O}$ --

Please add the following claims after claim 3 in column 46:

Claim 4. The organodithiocyclopentane according to claim 2 which is methyl 7,13-dithia-9-hydroxyprostanoate.

Claim 5. The organodithiocyclopentane according to claim 2 which is methyl 7,13-dithia-11-hydroxyprostanoate.

Claim 6. The organodithiocyclopentane according to claim 2 which is methyl 7,13-dithia-9,15-dihydroxy-15-methyl-prostanoate.

Claim 7. The organodithiocyclopentane according to claim 2 which is methyl 7,13-dithia-11-hydroxy-16-phenyl-17,18,19,20-tetranorprostanoate.

Signed and Sealed this

Eighteenth Day of March 1980

[SEAL]

Attest:

SIDNEY A. DIAMOND

Attesting Officer          Commissioner of Patents and Trademarks